US007186727B2

(12) United States Patent
Dhar et al.

(10) Patent No.: US 7,186,727 B2
(45) Date of Patent: Mar. 6, 2007

(54) PYRIDYL-SUBSTITUTED SPIRO-HYDANTOIN COMPOUNDS AND USE THEREOF

(75) Inventors: T. G. Murali Dhar, Newtown, PA (US); Michele Launay, Rueil Malmaison (FR); Dominique Potin, Epone (FR); Scott Hunter Watterson, Pennington, NJ (US); Zili Xiao, West Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/301,454

(22) Filed: Dec. 13, 2005

(65) Prior Publication Data

US 2006/0148836 A1  Jul. 6, 2006

Related U.S. Application Data

(60) Provisional application No. 60/636,012, filed on Dec. 14, 2004.

(51) Int. Cl.
*A61K 31/4439* (2006.01)
*C07D 401/14* (2006.01)
(52) U.S. Cl. .................. 514/278; 546/15; 546/274.4; 514/341
(58) Field of Classification Search ............... 514/278, 514/341; 546/15, 274.4
See application file for complete search history.

(56) References Cited

U.S. PATENT DOCUMENTS

| 4,931,444 | A | 6/1990 | Van Wauwe et al. |
| 5,346,913 | A | 9/1994 | Hsu et al. |
| 5,434,176 | A | 7/1995 | Claussner et al. |
| 5,750,553 | A | 5/1998 | Claussner et al. |
| 6,087,509 | A | 7/2000 | Claussner et al. |
| 6,977,267 | B2 | 12/2005 | Dhar et al. |
| 2006/0074099 | A1 | 4/2006 | DelMonte et al. |

FOREIGN PATENT DOCUMENTS

| WO | WO 98/39303 | 9/1998 |
| WO | WO 99/11258 | 3/1999 |
| WO | WO 99/20617 | 4/1999 |
| WO | WO 99/20618 | 4/1999 |
| WO | WO 99/49856 | 10/1999 |
| WO | WO 00/21920 | 4/2000 |
| WO | WO 00/39081 | 7/2000 |
| WO | WO 00/48989 | 8/2000 |
| WO | WO 00/59880 | 10/2000 |
| WO | WO 01/06984 | 2/2001 |
| WO | WO 01/07044 | 2/2001 |
| WO | WO 01/07048 | 2/2001 |
| WO | WO 01/07052 | 2/2001 |
| WO | WO 01/07440 | 2/2001 |
| WO | WO 01/30781 | 5/2001 |
| WO | WO 01/51508 | 7/2001 |
| WO | WO 01/58853 | 8/2001 |
| WO | WO 02/02522 | 1/2002 |
| WO | WO 02/02539 | 1/2002 |
| WO | WO 02/28832 | 4/2002 |
| WO | WO 02/42294 | 5/2002 |
| WO | WO 02/44181 | 6/2002 |
| WO | WO 02/059114 | 8/2002 |
| WO | WO 02/096426 | 12/2002 |
| WO | WO 03/029245 | 4/2003 |

OTHER PUBLICATIONS

Arseniyadis, S. et al., "Kinetic Resolution of Amines: A Highly Enantioselective and Chemoselective Acetylating Agent with a Unique Solvent-Induced Reversal of Stereoselectivity", Angew. Chem. Int. Ed., vol. 43, pp. 3314-3317 (2004).
Diamond, M.S. et al., "The dynamic regulation of integrin adhesiveness", Current Biology, vol. 4, No. 6, pp. 506-517 (1994).
Joucla, M. et al., "Pyrrolidines from α-Amino-Acids Derivatives", Tetrahedron Letters, vol. 26, No. 23, pp. 2775-2778 (1985).
Sanfilippo, P.J. et al., "Novel Thiazole Based Heterocycles as Inhibitors of LFA-1/ICAM-1 Mediated Cell Adhesion", J. Med. Chem. vol. 38, No. 7, pp. 1057-1059 (1995).
Tsuge, O. et al., "Amino Acid Approach as a General Route to Nonstabilized Azomethine Ylides. Facile Generation of Parent Methaniminium Methylide and Its 1-Mono- and 1,1-Disubstituted Derivatives", Chemistry Letters, pp. 973-976 (1986).
Tsuge, O. et al., "Simple Generation of Nonstabilized Azomethine Ylides through Decarboxylative Condensation of α-Amino Acids with Carbonyl Compounds via 5-Oxazolidinone Intermediates", Bull. Chem. Soc. Jpn., vol. 60, pp. 4079-4089 (1987).

*Primary Examiner*—Charanjit S. Aulakh
(74) *Attorney, Agent, or Firm*—Laurelee A. Duncan

(57) ABSTRACT

A class of substituted spiro-hydantoin compounds (II) having the formula:

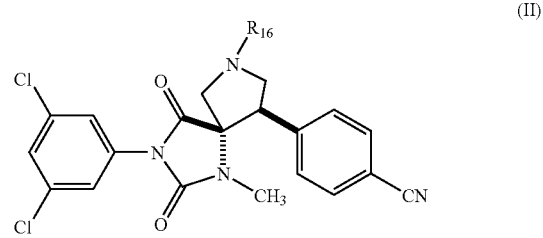

(II)

its pharmaceutically acceptable salts, enantiomers, solvates, or prodrugs thereof, wherein $R_{16}$ is a substituted pyridinyl group, as defined herein, is provided. Pharmaceutical compositions and methods of treating anti-inflammatory and/or immune diseases with the pyridyl-substituted spiro-hydantoin compounds are also objectives of this invention.

8 Claims, 5 Drawing Sheets

PYRIDYL-SUBSTITUTED SPIRO-HYDANTOIN COMPOUNDS AND USE THEREOF

This application claims priority from U.S. Provisional Application No. 60/636,012, filed Dec. 14, 2004, incorporated in its entirety herein by reference.

FIELD OF THE INVENTION

The present invention provides a class of pyridyl-substituted spiro-hydantoin compounds having unexpectedly desirable pharmacological characteristics. Pharmaceutical compositions and methods of treating anti-inflammatory and/or immune diseases with the pyridyl-substituted spiro-hydantoin compounds are also objectives of this invention.

BACKGROUND OF THE INVENTION

A key event in an immune response involves the migration of leukocytes to a disease site. During an inflammatory response, leukocytes are recruited to the site of injury and are extravasated by a series of cellular interactions involving cell-cell and cell-substrate adhesion. The administration of compounds that inhibit these cellular interactions of leukocytes provides a route for treating inflammatory or immune diseases.

One family of molecules that serves an important adhesive function is integrins. Integrins are expressed on cell surfaces and function in cell-cell and cell-substrate adhesion. Integrins are alpha-beta heterodimers: each integrin has an alpha ($\alpha$) subunit non-covalently bound to a beta ($\beta$) subunit. There are four known integrins having a $\beta_2$ or CD18 subunit, which comprise the CD11/CD18 integrin sub-family, namely, Lymphocyte Function-associated Antigen 1 (LFA-1) (CD11a/CD18 or $\alpha_L\beta_2$); Macrophage Antigen 1 (Mac-1) (CD11b/CD18 or $\alpha_M\beta_2$); p150,95 (CD11c/CD18 or $\alpha_X\beta_2$); and $\alpha_D\beta_2$. The CD11/CD18 family of integrins is also referred to as Leukointegrins as they are expressed on the surface of various leukocyte cells, and they mediate a number of inflammation-related cellular interactions. See Diamond et al., "The Dynamic Regulation of Integrin Adhesiveness," *Current Biology*, Vol. 4 (1994) at pp. 506–532.

When activated, the integrins bind to extracellular ligands and induce adhesion. Ligands to LFA-1 and Mac-1 comprise the intercellular adhesion molecule (ICAM) ICAM-1. The primary CD11/CD18 integrin is LFA-1, which also binds with ICAM-2 and ICAM-3. The interaction between the CD18 integrins, particularly LFA-1, and ICAMs mediates antigen presentation, T-cell proliferation, and adhesion between the endothelium and activated leukocytes, which is necessary for leukocytes to migrate from the circulatory system into tissue. Compounds inhibiting CD18 integrins, ICAMs, and/or the LFA-1:ICAM interaction have demonstrated a wide range of utilities in treating inflammatory or immune diseases. Compounds that reportedly inhibit LFA-1/ICAM for use as anti-inflammatory agents include thiadiazole-based compounds (see Intern. Pub. No. WO 99/20, 618, *"Thiadiazole Amides Useful as Anti-Inflammatory Agents"* filed by Pharmacia & Upjohn Co.; and WO 99/20, 617, also to Pharmacia and Upjohn); and thiazole compounds linked to phenyl and pyrazole rings (Sanfilippo et al., "Novel Thiazole Based Heterocycles as Inhibitors of LFA-1/ICAM-1 Mediated Cell Adhesion," *J. Med. Chem.*, Vol. 38 (1995) at pp.1057–1059). Small molecules that reportedly are antagonists to the binding of ICAMs with CD18 integrins include various benzylamines and 2-bromobenzoyl-tryptophan compounds (see Intern. Pub. No. WO99/49,856, *"Antagonists for Treatment of CD11/CD18 Adhesion Receptor Mediated Disorders,"* filed by Genentech, Inc.), and 1-(3,5 dichlorophenyl)imidazolidines (see Intern. Pub. No. WO98/39303, *"Small Molecules Useful in the Treatment of Inflammatory Disease,"* filed by Boehringer Ingelheim Pharmaceuticals, Inc. See also Boehringer patent applications WO 01/07052, WO 01/07048, WO 01/07044, WO 01/06984, and WO 01/07440). Hydantoin compounds are disclosed in Intern. Pub. No's WO 00/59880, WO 00/39081, WO 02/02522, and WO 02/02539 (all to Abbott Laboratories). LFA-1 antagonist compounds are also claimed in WO 02/059114 (to Genentech), WO 02/42294 (to Celltech), WO 01/51508 (to Science and Technology Corporation), WO 00/21920 and WO 01/58853 (both to Hoffmann-LaRoche), WO 99/11258, WO 00/48989 and WO 02/28832 (all to Novartis). Hydantoin compounds are disclosed in Intern. Pub. No. WO 01/30781 A2 (published May 3, 2001) to Tanabe Seiyaku Co. Ltd, "Inhibitors of $\alpha_L\beta_2$ Mediated Cell Adhesion," and in Intern. Pub. No. WO 02/44181 (published Jun. 6, 2002), "Hydantoin Compounds Useful as Anti-Inflammatory Agents", to the present assignee.

Accordingly, compounds that inhibit CD18 integrins, ICAMs, and/or the LFA-1:ICAM interaction could demonstrate a wide range of utilities in treating inflammatory or immune diseases. U.S. Patent Application Publication 2004/0009998 A1 (incorporated herein by reference and assigned to present applicant) discloses aryl or heteroaryl substituted spiro-hydantoin compounds that are antagonists of Leukointegrins and/or ICAMs, for example these compounds inhibit the LFA-1:ICAM interaction. The reference also discloses various processes to prepare these spiro-hydantoins, such as a multistep synthesis that includes the introduction and subsequent removal of protecting groups.

It is desirable to find new compounds with improved pharmacological characteristics compared with known inhibitors of CD18 integrins, ICAMS, and/or the LFA-1:ICAM interaction. For example, it is preferred to find new compounds that demonstrate improved inhibition of the LFA-1:ICAM interaction. It is also desirable and preferable to find compounds with advantageous and improved pharmacological characteristics. Such characteristic include, but are not limited to: (a) pharmaceutical properties; (b) dosage requirements; (c) factors which decrease blood concentration peak-to-trough characteristics; (d) factors, such as increased metabolic stability, that increase the concentration of active drug at the receptor; (e) factors that decrease the liability for clinical drug-drug interactions; (f) factors that decrease the potential for adverse side-effects; and/or (g) factors that improve manufacturing costs or feasibility.

It is also desirable in the art to provide new and/or improved processes to prepare substituted spiro-hydantoin compounds. Such processes may be characterized, without limitation, by a) facile adaptation to larger scale production, such as pilot plant or manufacturing scales; b) process steps and/or techniques enabling improvements in the purity of intermediates and/or final compounds; and/or c) fewer process steps.

SUMMARY OF THE INVENTION

The present invention provides substituted spiro-hydantoin compounds (II) of formula:

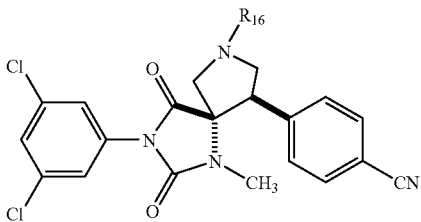

(II)

its enantiomers, or pharmaceutically-acceptable salts, solvates, or prodrugs thereof, in which:

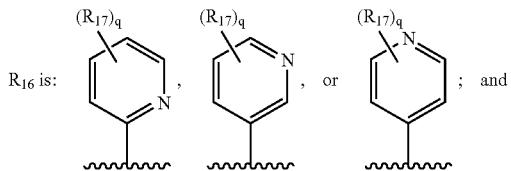

$R_{17}$ and q are as defined herein below. It has been discovered that compounds of formula II, particularly compounds of formula IId, have several desirable pharmacological characteristics. Such characteristics include, without limit, high metabolic stability and/or a low risk of drug-drug interactions as demonstrated by testing in the microsomal liver and CYP assays, respectively, which are described herein, infra.

The present invention is also directed to pharmaceutical compositions, useful in treating immune or inflammatory diseases comprising compounds according to formula II, and pharmaceutically-acceptable carriers or diluents. The invention further relates to methods of treating immune or inflammatory diseases comprising administering to a patient in need of such treatment a therapeutically-effective amount of a compound according to formula II.

DETAILED DESCRIPTION OF THE INVENTION

Figure 1:
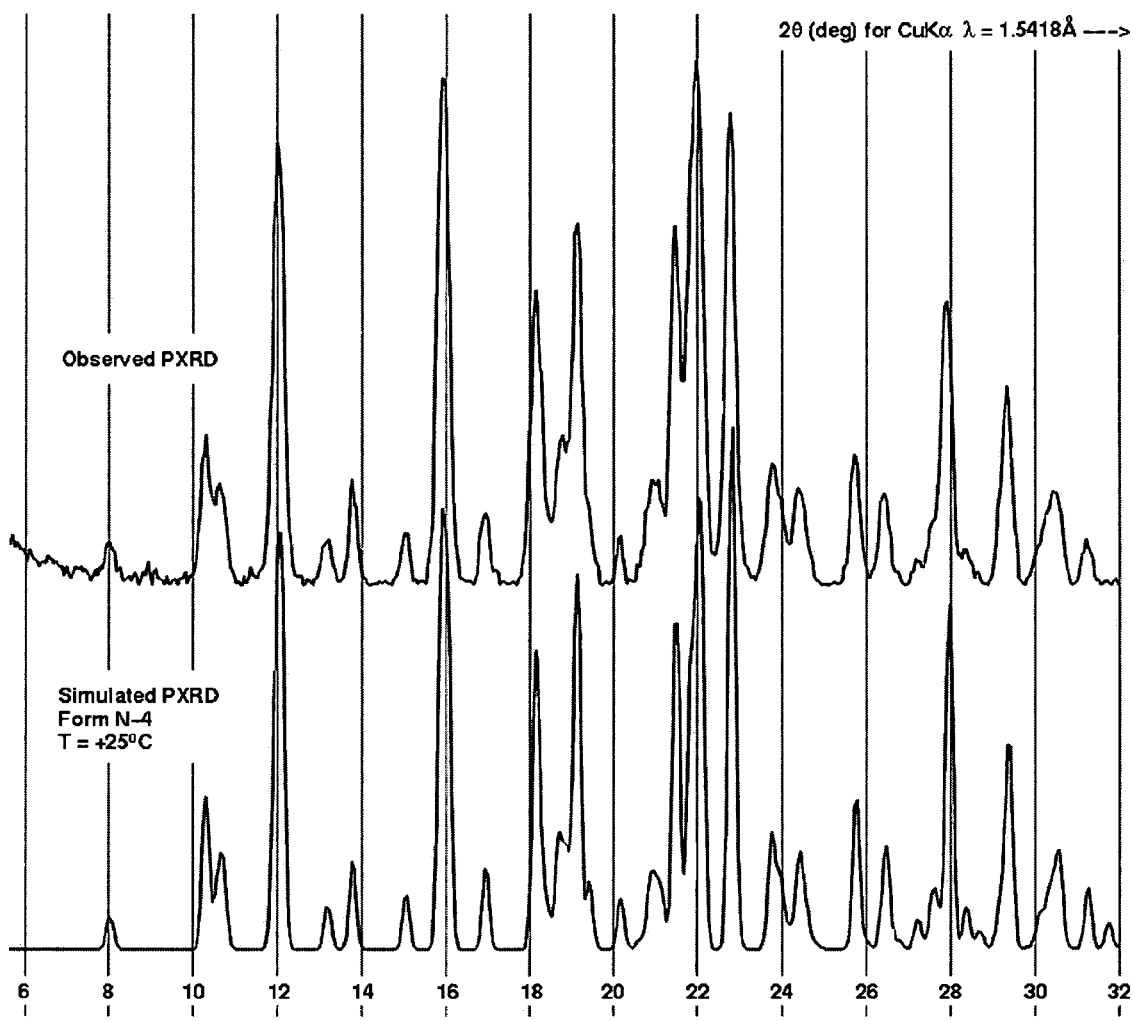
FIG. 1. shows observed and simulated powdered x-ray diffraction patterns (CuKα λ=1.5418 Å at T=25° C.) of the N-4 crystalline form of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid.
Figure 2:
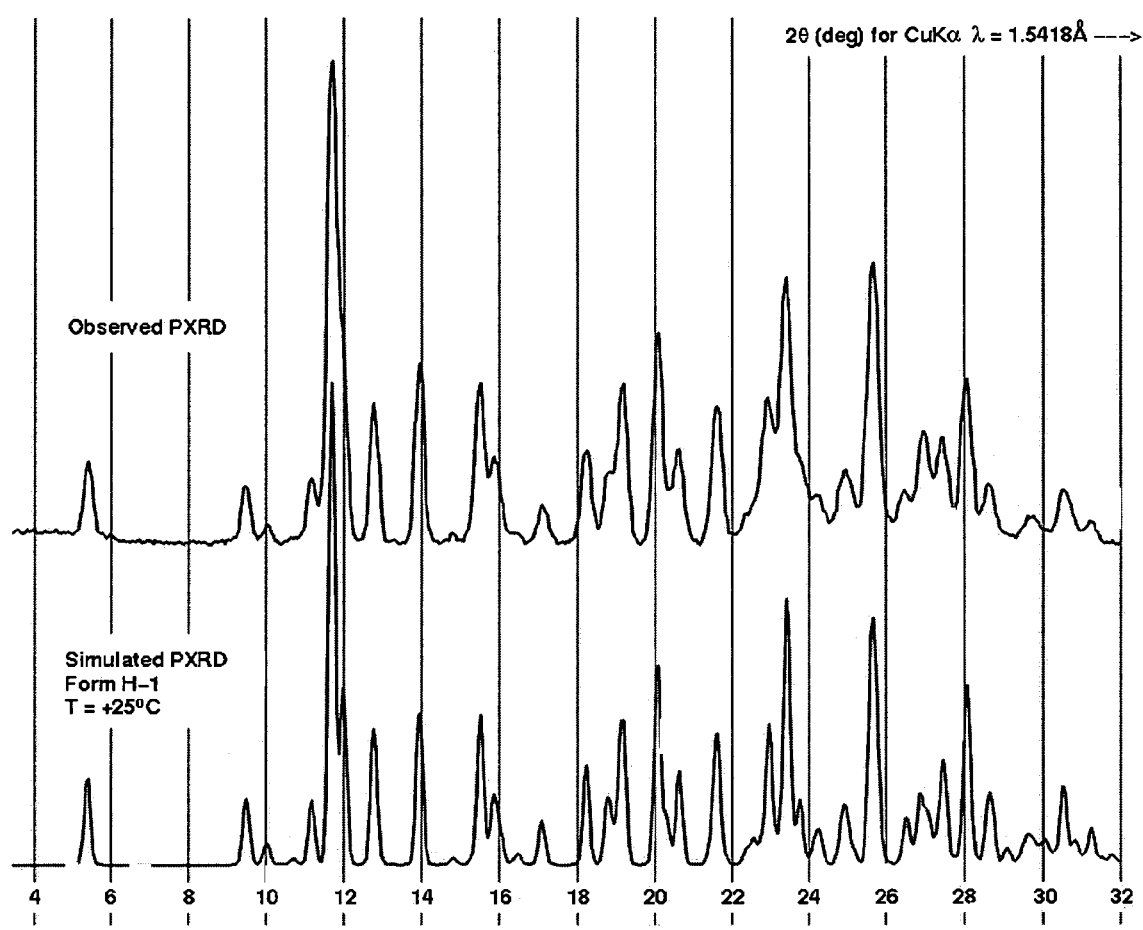
FIG. 2. shows observed and simulated powdered x-ray diffraction patterns (CuKα λ=1.5418 Å at T=25° C.) of the monohydrate crystalline form of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid (H-1).
Figure 3:
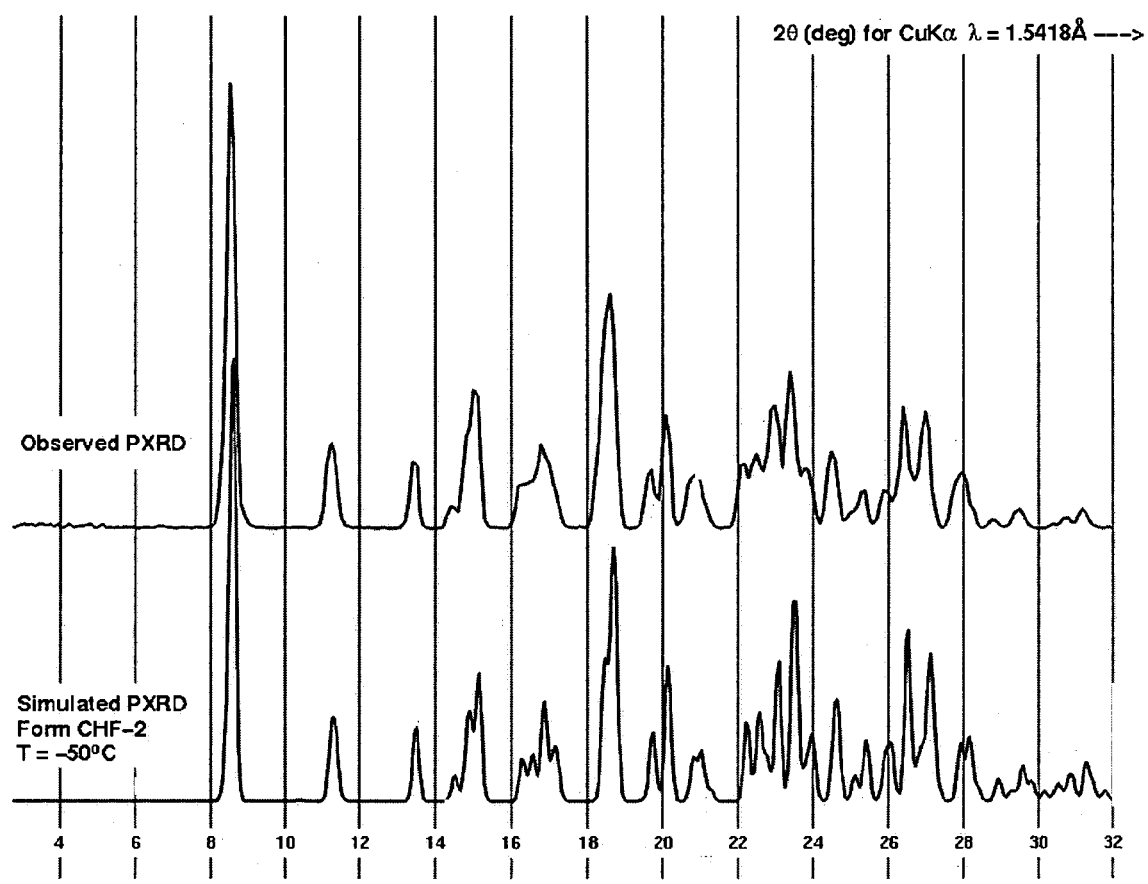
FIG. 3. shows observed and simulated powdered x-ray diffraction patterns (CuKα λ=1.5418 Å at T=−50° C.) of the chloroform solvate crystalline form of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid (CHF-2).
Figure 4:
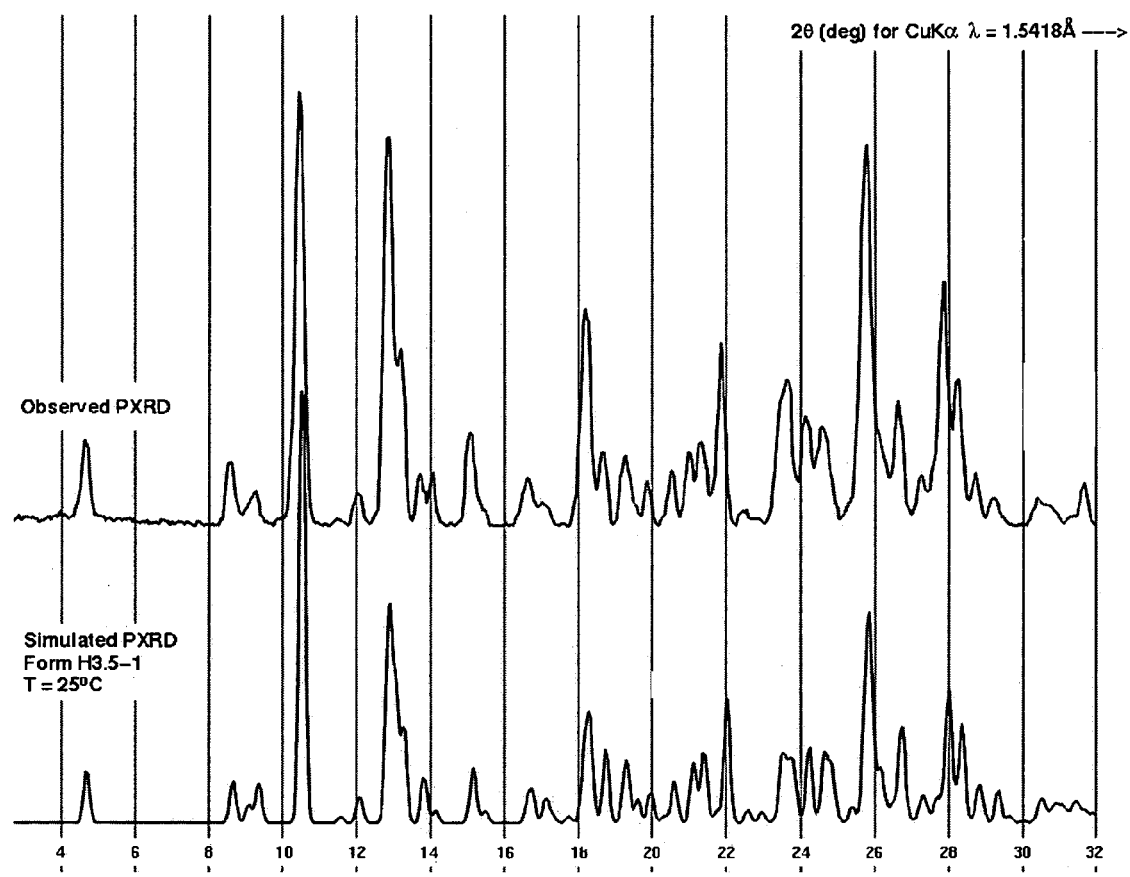
FIG. 4. shows observed and simulated powdered x-ray diffraction patterns (CuKα λ=1.5418 Å T=25° C.) of a crystalline hydrate form of the HCl salt of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid (H3.5–1).
Figure 5:
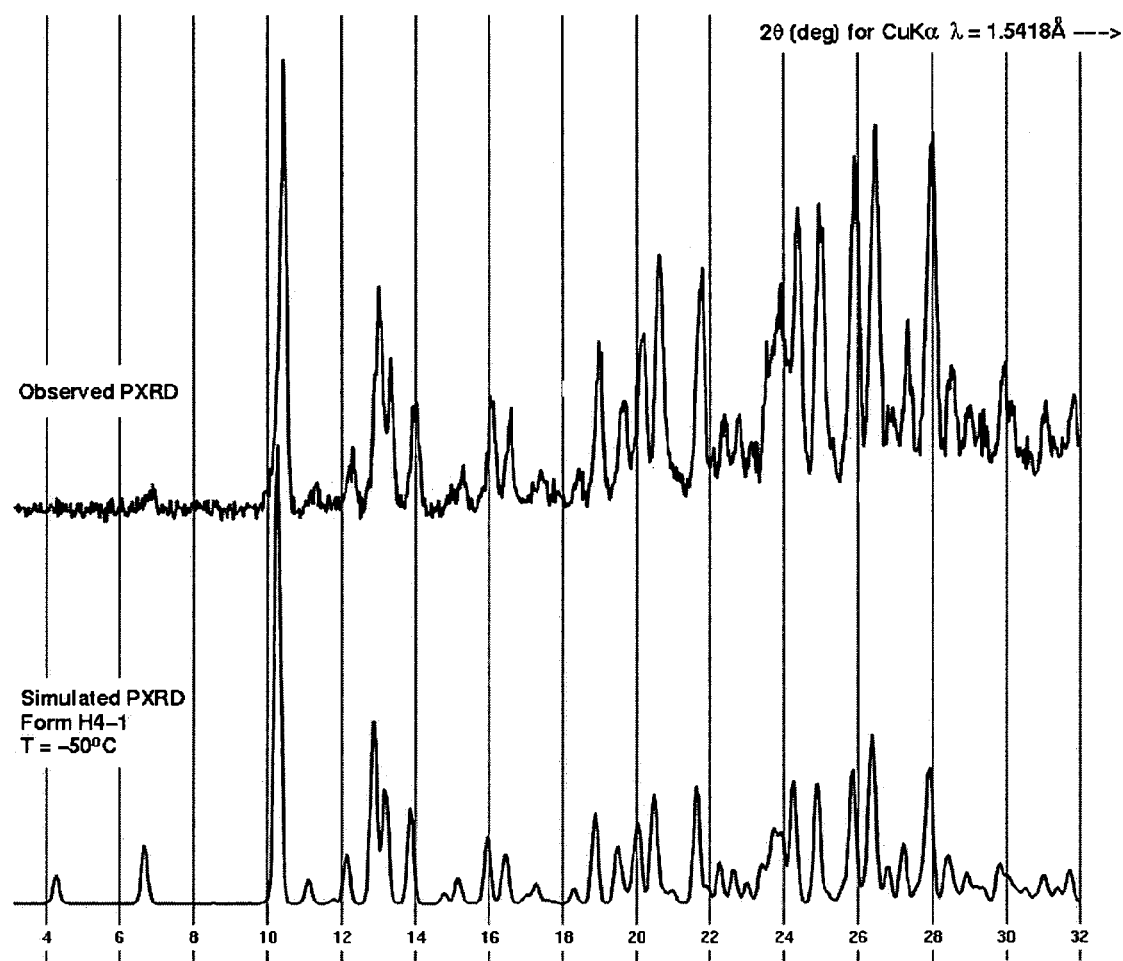
FIG. 5. shows observed and simulated powdered x-ray diffraction patterns (CuKα λ=1.5418 Å at T=−50° C.) of the crystalline form of the hemi-HCl salt of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid (H4–1).

The following are definitions of terms used in this specification and appended claims. The initial definition provided for a group or term herein applies to that group or term throughout the specification and claims, individually or as part of another group, unless otherwise indicated.

The term "alkyl" refers to a straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy ($C_{0-2}$)alkyl or ($C_{0-2}$)hydroxyalkyl includes hydroxy, hydroxymethyl and hydroxyethyl.

The term "substituted alkyl" refers to an alkyl group as defined above having one, two, or three substituents selected from halo (e.g., trifluoromethyl), alkenyl, substituted alkenyl, alkynyl, nitro, cyano, oxo (=O), —$OR_a$, —$SR_a$, (=S), —$NR_aR_b$, —N(alkyl)$_3^+$, —$NR_aSO_2$, —$NR_aSO_2R_c$, —$SO_2R_c$, —$SO_2NR_aR_b$, —$SO_2NR_aC(=O)R_b$, —$SO_3H$, —$PO(OH)_2$, —$C(=O)R_a$, —$CO_2R_a$, —$C(=O)NR_aR_b$, —$C(=O)(C_{1-4}$alkylene)$NR_aR_b$, —$C(=O)NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$ and $R_b$ are selected from hydrogen, alkyl, alkenyl, —$CO_2H$, —$CO_2$(alkyl), $C_{3-7}$cycloalkyl, phenyl, benzyl, phenylethyl, napthyl, a four to seven membered heterocyclo, and a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) selected from ($C_{1-6}$)alkyl, ($C_{2-6}$)alkenyl, hydroxy, halogen, cyano, nitro, $CF_3$, —O($C_{1-6}$alkyl), —$OCF_3$, —C(=O)H, —C(=O)($C_{1-6}$alkyl), —$CO_2H$, —$CO_2(C_{1-6}$alkyl), —$NHCO_2(C_{1-6}$alkyl), —S($C_{1-6}$alkyl), —$NH_2$, —NH($C_{1-6}$alkyl), —N($C_{1-6}$alkyl)$_2$, —N($CH_3$)$_3^+$, —$SO_2(C_{1-6}$alkyl), —C(=O)($C_{1-4}$alkylene)$NH_2$, —C(=O)($C_{1-4}$alkylene)NH(alkyl), —C(=O)($C_{1-4}$alkylene)N($C_{1-4}$alkyl)$_2$, $C_{3-7}$cycloalkyl, phenyl, benzyl, phenylethyl, phenyloxy, benzyloxy, napthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below.

One skilled in the field will understand that, when the designation "$CO_2$" is used herein, this is intended to refer to the group

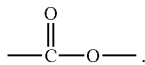

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl.

The term "alkenyl" refers to straight or branched chain hydrocarbon groups having 2 to 12 carbon atoms and at least one double bond. Alkenyl groups of 2 to 6 carbon atoms and having one double bond are most preferred.

The term "alkynyl" refers to straight or branched chain hydrocarbon groups having 2 to 12 carbon atoms and at least one triple bond. Alkynyl groups of 2 to 6 carbon atoms and having one triple bond are most preferred.

The term "alkylene" refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1–8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(═O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —CH$_2$—NH—, —S—CH$_2$)$_{1-5}$NH—CH$_2$—, —O—(CH$_2$)$_{1-5}$S(═O)—CH$_2$—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, —CH$_2$—O—CH$_2$— and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, and -A$_1$-Q-A$_2$-R$_{16}$, wherein A$_1$ is a bond, $C_{1-2}$alkylene, or $C_{2-3}$alkenylene; Q is a bond, —C(═O)—, —C(═O)NR$_d$—, —C(═S)NR$_d$—, —SO$_2$—, —SO$_2$NR$_d$—, —CO$_2$—, or —NR$_d$CO$_2$—; A$_2$ is a bond, $C_{1-3}$alkylene, $C_{2-3}$alkenylene, —C$_{1-4}$alkylene-NR$_d$—, —C$_{1-4}$alkylene-NR$_d$C(═O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; each R$_{16}$ is independently hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that R$_{16}$ is not hydrogen when A$_1$, Q, and A$_2$ are each bonds. When R$_{16}$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —CH$_2$—NH$_2$, —NH—CH$_3$, —(CH$_2$)$_2$—NH$_2$—NH—CH$_2$—CH$_3$, —CH$_2$—NH—CH$_3$, and —N—(CH$_3$)$_2$. A lower aminoalkyl comprises an aminoalkyl having one to four carbon atoms. "Amino" refers to the group NH$_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

It should be understood that the selections for alkoxy, thioalkyl, and aminoalkyl will be made by one skilled in the field to provide stable compounds.

The term "acyl" refers to a carbonyl group linked to an organic radical, more particularly, the group —C(═O)R$_e$, as well as the bivalent groups —C(═O)— or —C(═O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in alkene compound (III) and substituted spiro-hydantoin compounds (I) and (II), when it is recited that G can be "acyl," this is intended to encompass a selection for G of —C(=O)— and also the groups —C(=O)R$_e$— or —R$_e$C(=O)—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" refers to a carboxy group

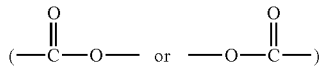

linked to an organic radical (CO$_2$R$_e$), as well as the bivalent groups —CO$_2$—, —CO$_2$R$_e$— which are linked to organic radicals in alkene compound (III) and substituted spiro-hydantoin compounds (I) and (II), wherein R$_e$ is as defined above for acyl. The organic radical to which the carboxy group is attached may be monovalent (e.g., —CO$_2$-alkyl or —OC(=O)alkyl), or bivalent (e.g., —CO$_2$-alkylene, —OC(=O)alkylene, etc.). Accordingly, in alkene compound (III) and substituted spiro-hydantoin compounds (I) and (II), when it is recited that G can be "alkoxycarbonyl," this is intended to encompass a selection for G of —CO$_2$— and also the groups —CO$_2$R$_e$— or —R$_e$CO$_2$—, wherein in this instance, the group R$_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" refers to the group —C(=O)NR$_a$R$_b$, wherein the groups R$_a$ and R$_b$ are defined as recited above in the definition for substituted alkyl groups.

The term "sulfonyl" refers to a sulphoxide group linked to an organic radical, more particularly, the monovalent group —S(O)$_{1-2}$—R$_e$, or the bivalent group —S(O)$_{1-2}$— linked to organic radicals. Accordingly, in alkene compound (III) and the substituted spiro-hydantoin compounds (I) and (II), when it is recited that G can be "sulfonyl," this is intended to encompass a selection for G of —S(=O)— or —SO$_2$— as well as the groups —S(=O)R$_e$—, —R$_e$S(=O)—, —SO$_2$R$_e$—, or —R$_e$SO$_2$—, wherein in thi instance, the group R$_e$ will be selected from those recited above for acyl and alkoxycarbonyl groups.

The term "sulfonamidyl" refers to the group —S(O)$_2$NR$_a$R$_b$, wherein R$_a$ and R$_b$ are as defined above for substituted alkyl groups. Additionally, the sulfonamidyl group may be bivalent, in which case one of the groups R$_a$ and R$_b$ will be a bond. Thus, in alkene compound (III) and substituted spiro-hydantoin compound (I) and (II), when it is stated that G may be sulfonamidyl, it is intended to mean that G is a group —S(O)$_2$NR$_a$—.

The term "cycloalkyl" refers to a fully saturated or partially saturated cyclic hydrocarbon group containing from 1 to 4 rings and 3 to 8 carbons per ring. Exemplary fully saturated cycloalkyl groups include cyclopropyl, cyclobutyl, cyclopentyl, and cyclohexyl. Exemplary partially saturated cycloalkyl groups include cyclobutenyl, cyclopentenyl, and cyclohexenyl. "Substituted cycloalkyl" refers to a cycloalkyl group substituted with one or more substituents, preferably 1 to 4 substituents, at any available point of attachment. Exemplary substituents include, but are not limited to, halogen, trifluoromethyl, trifluoromethoxy, alkyl, substituted alkyl, alkenyl, substituted alkenyl, alkynyl, nitro, cyano, oxo (=O), —OR$_a$, —SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, —SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$)alkyl, (C$_{2-4}$)alkenyl, halogen, hydroxy, cyano, nitro, CF$_3$, —O(C$_{1-4}$alkyl), —OCF$_3$, —C(=O)H, —C(=O)(C$_{1-4}$alkyl), —CO$_2$H, —CO$_2$(C$_{1-4}$alkyl), —NHCO$_2$(C$_{1-4}$alkyl), —S(C$_{1-4}$alkyl), —NH$_2$, —NH(C$_{1-4}$alkyl), —N(C$_{1-4}$alkyl)$_2$, —N(C$_{1-4}$alkyl)$_3^+$, —SO$_2$(C$_{1-4}$alkyl), —C(=O)(C$_{1-4}$alkylene)NH$_2$, —C(=O)(C$_{1-4}$alkylene)NH(alkyl), and/or —C(=O)(C$_{1-4}$alkylene)N(C$_{1-4}$alkyl)$_2$.

The term "cycloalkyl" includes cyclopropyl, cyclobutyl, cyclopentyl, cyclohexyl, cycloheptyl, cyclooctyl, etc., as well as the following ring systems,

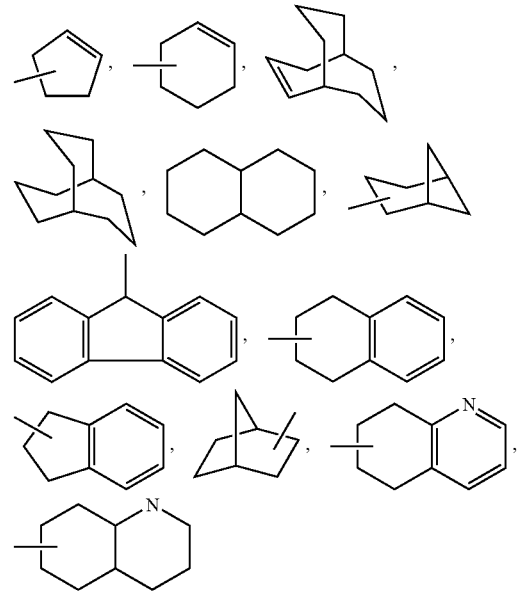

and the like, which optionally may be substituted at any available atoms of the ring(s). Preferred cycloalkyl groups include cyclopropyl, cyclobutyl, cyclopentyl, cyclohexyl,

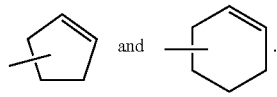

The term "halo" or "halogen" refers to fluoro, chloro, bromo, and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The term "aryl" refers to phenyl, biphenyl, 1-naphthyl and 2-naphthyl. The term "aryl" includes such rings having zero, one, two or three substituents selected from halogen, trifluoromethyl, trifluoromethoxy, alkyl, substituted alkyl, alkenyl, substituted alkenyl, alkynyl, nitro, cyano, —OR$_a$, —SR$_a$, (=S), —NR$_a$R$_b$, —N(alkyl)$_3^+$, —NR$_a$SO$_2$, —NR$_a$SO$_2$R$_c$, —SO$_2$R$_c$—SO$_2$NR$_a$R$_b$, —SO$_2$NR$_a$C(=O)R$_b$, —SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), —NHCO$_2$(C$_{1-4}$alkyl), —S(C$_{1-4}$alkyl), —NH$_2$, —NH(C$_{1-4}$alkyl), —N(C$_{1-4}$alkyl)$_2$, —N(C$_{1-4}$alkyl)$_3^+$, —SO$_2$(C$_{1-4}$alkyl), —C(=O)(C$_{1-4}$alkylene)NH$_2$, —C(=O)(C$_{1-4}$alkylene)NH(alkyl), and/or —C(=O)(C$_{1-4}$alkylene)N(C$_{1-4}$alkyl)$_2$.

Thus, examples of aryl groups include:

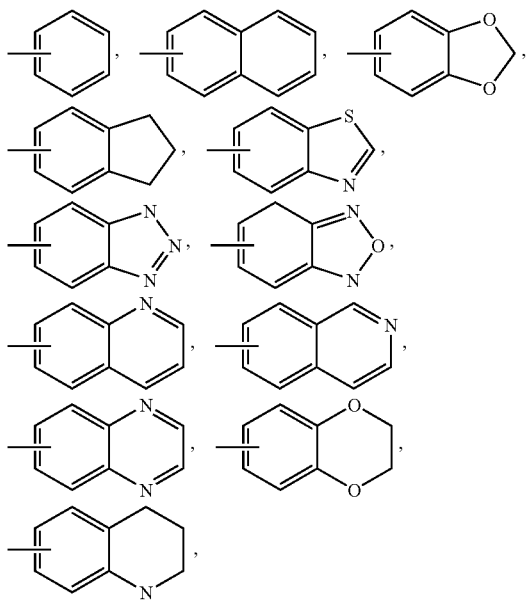

and the like, which optionally may be substituted at any available carbon or nitrogen atom. A preferred aryl group is optionally-substituted phenyl.

The terms "heterocyclo" or "heterocyclic" refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from halogen, trifluoromethyl, trifluoromethoxy, alkyl, substituted alkyl, alkenyl, substituted alkenyl, alkynyl, nitro, cyano, oxo (=O), —OR$_a$, —SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, —SO$_3$H, —PO(OH)$_2$, —C(=O)R$_a$, —CO$_2$R$_a$, —C(=O)NR$_a$R$_b$, —NR$_a$C(=O)R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$, R$_b$ and R$_c$ are as defined above for substituted alkyl groups, and are also in turn optionally substituted as recited above. When a heterocyclo is substituted with a further ring, said ring in turn is optionally substituted with one to two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), —NHCO$_2$(C$_{1-4}$alkyl), —S(C$_{1-4}$alkyl), —NH$_2$, —NH(C$_{1-4}$alkyl), —N(C$_{1-4}$alkyl)$_2$, —N(C$_{1-4}$alkyl)$_3^+$, —SO$_2$(C$_{1-4}$alkyl), —C(=O)(C$_{1-4}$alkylene)NH$_2$, —C(=O)(C$_{1-4}$alkylene)NH(alkyl), and/or —C(=O)(C$_{1-4}$alkylene)N(C$_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Suitable heterocyclo groups in alkene compound (III) and substituted spiro-hydantoin compounds (I) and (II), include

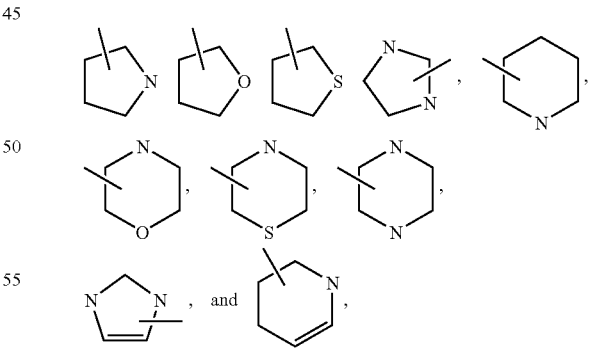

which optionally may be substituted.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from halogen, trifluoromethyl, trifluoromethoxy, alkyl, substituted alkyl, alkenyl, substituted alkenyl, alkynyl, nitro, cyano, —OR$_a$, —SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, —SO$_3$H, —PO(OH)$_2$, —C(=O)R$_a$, —CO$_2$R$_a$, —C(=O)(C$_{1-4}$alkylene)NR$_a$R$_b$, —C(=O) NR$_a$R$_b$, —C(=O)NR$_a$(SO$_2$)R$_b$, —CO$_2$(C$_{1-4}$alkylene) NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above. When a heteroaryl is substituted with a further ring, said ring in turn is optionally substituted with one to two of (C$_{1-4}$)alkyl, (C$_{2-4}$)alkenyl, halogen, hydroxy, cyano, nitro, CF$_3$, —O(C$_{1-4}$alkyl), —OCF$_3$, —C(=O)H, —C(=O)(C$_{1-4}$alkyl), —CO$_2$H, —CO$_2$(C$_{1-4}$alkyl), —NHCO$_2$(C$_{1-4}$alkyl), —S(C$_{1-4}$alkyl), —NH$_2$, —NH(C$_{1-4}$alkyl), —N(C$_{1-4}$alkyl)$_2$, —N(C$_{1-4}$alkyl)$_3^+$, —SO$_2$(C$_{1-4}$alkyl), —C(=O)(C$_{1-4}$alkylene)NH$_2$, —C(=O) (C$_{1-4}$alkylene)NH(alkyl), and/or —C(=O)(C$_{1-4}$alkylene)N (C$_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In alkene compound (III) and substituted spiro-hydantoin compounds (I) and (II), suitable heteroaryl groups include

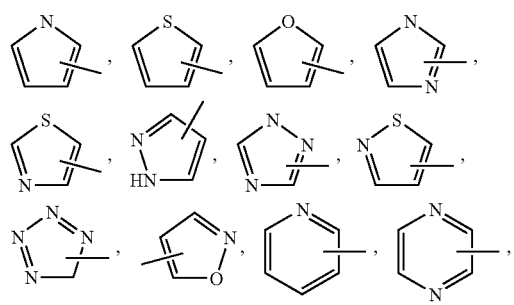

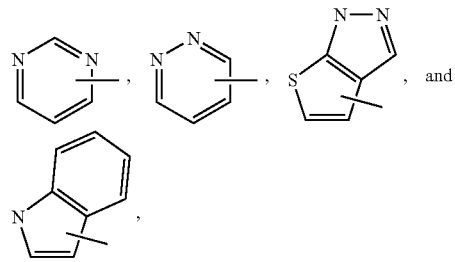

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0–2, substituents selected from those recited above for the aryl, cycloalkyl, heterocyclo, and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds useful as pharmaceutically-acceptable compounds and/or intermediate compounds useful in making pharmaceutically-acceptable compounds.

The compounds of formulae I to IV can form salts which are also within the scope of this invention. Unless otherwise indicated, reference to a compound of one of formulae I to IV is understood to include reference to salts thereof. The term "salt(s)" denotes acidic and/or basic salts formed with inorganic and/or organic acids and bases. In addition, the term "salt(s) may include zwitterions (inner salts), e.g., when a compound of formulae I to IV contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formulae I to IV may be formed, for example, by reacting a compound of the formulae I to IV with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

Prodrugs and solvates of the compounds of formulae I and II are also contemplated. The term "prodrug" denotes a compound which, upon administration to a subject, undergoes chemical conversion by metabolic or chemical processes to yield a compound of the formulae I or II, and/or a salt and/or solvate thereof. For example, compounds containing a carboxy group can form physiologically hydrolyzable esters which serve as prodrugs by being hydrolyzed in the body to yield formulae I or II compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formulae II and III include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyloxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

The compounds of the formulae I and II, and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. When diastereomeric products are prepared, they can be separated by conventional methods for example, chromatographic or fractional crystallization. The substituted spiro-hydantoin compounds (I) and (II) may be in the free or hydrate form.

Compounds of the formulae I and II may also have prodrug forms. Any compound that will be converted in vivo to provide the bioactive agent (i.e., the compound for formula I or II) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 112, pp. 309–396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews*, Vol. 8, pp. 1–38 (1992), each of which is incorporated herein by reference.

It should further be understood that solvates (e.g., hydrates) of the compounds of Formulae I and II are also within the scope of the present invention. Methods of solvation are generally known in the art.

As used herein "polymorph" refers to crystalline forms having the same chemical composition but different spatial arrangements of the molecules, atoms, and/or ions forming the crystal.

As used herein "solvate" refers to a crystalline form of a molecule, atom, and/or ions that further comprises molecules of a solvent or solvents incorporated into the crystalline structure. An example of a solvate is a hydrate, which is a crystalline form comprising water. The solvent molecules in the solvate may be present in a regular arrangement and/or a non-ordered arrangement. The solvate may comprise either a stoichiometric or nonstoichiometric amount of the solvent molecules. For example, a solvate with a nonstoichiometric amount of solvent molecules may result from partial loss of solvent from the solvate.

The present invention provides a substituted spiro-hydantoin compound (II) according to formula:

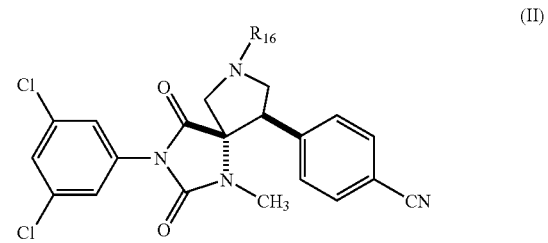

(II)

its enantiomers, or pharmaceutically-acceptable salts, solvates, or prodrugs thereof, in which:

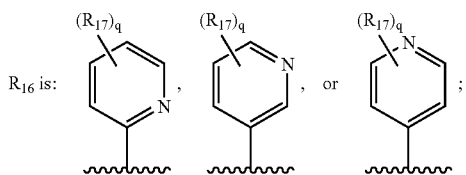

each $R_{17}$ is independently —$OR_{18}$, —$NR_{18}R_{19}$, —$C(=O)R_{18}$, —$CO_2R_{18}$, —$C(=O)NR_{18}R_{19}$, —$NR_{18}C(=O)R_{19}$, —$NR_{18}C(=O)OR_{19}$, —$S(O)_pR_{19}$, —$NR_{18}SO_2R_{19}$, and/or —$SO_2NR_{18}R_{19}$; preferably each $R_{17}$ is independently —$OR_{18}$, —$C(=O)R_{18}$, —$CO_2R_{18}$, and/or —$C(=O)NR_{18}R_{19}$; and more preferably at least one $R_{17}$ is —$CO_2R_{18}$;

$R_{18}$ and $R_{19}$ are independently hydrogen, alkyl, substituted alkyl, cycloalkyl, and/or substituted cycloalkyl;

q is 1, 2, or 3; and p is 1 or 2.

As used herein, the substituted spiro-hydantoin compound (II) represents either enantiomer of the substituted spiro-hydantoin compound (II) or a mixture in any ratio of the enantiomers, including a racemic mixture of the enantiomers. The enantiomers of the substituted spiro-hydantoin compound (II) are represented by substituted spiro-hydantoin compound (IIa) of formula:

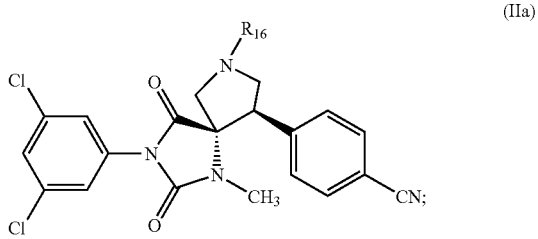

(IIa)

and substituted spiro-hydantoin compound (IIb) of formula:

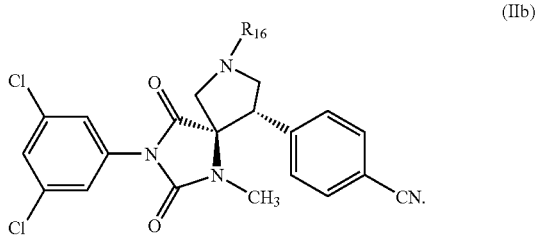

(IIb)

The substituted spiro-hydantoin compound (IIa) is preferred.

In one embodiment, the substituted spiro-hydantoin compound (II) is provided wherein:

each $R_{17}$ is independently —$OR_{18}$, —$C(=O)R_{18}$, —$CO_2R_{18}$, and/or —$C(=O)NR_{18}R_{19}$; preferably at least one $R_{17}$ is —$CO_2R_{18}$; and more preferably at least one $R_{17}$ is —$CO_2H$;

$R_{18}$ and $R_{19}$ are independently hydrogen, alkyl, and/or substituted alkyl; and $R_{16}$ and q are defined hereinabove.

In this embodiment, the substituted spiro-hydantoin compound (II) is preferably the enantiomer represented by the substituted spiro-hydantoin compound (IIa).

In a different embodiment, the substituted spiro-hydantoin compound (II) is provided wherein:

each $R_{17}$ is independently —$OR_{18}$, —$C(=O)R_{18}$, —$CO_2R_{18}$, and/or —$C(=O)NR_{18}R_{19}$; preferably at least one $R_{17}$ is —$CO_2R_{18}$; and more preferably at least one $R_{17}$ is —$CO_2H$;

$R_{18}$ and $R_{19}$ are independently hydrogen, alkyl, and/or substituted alkyl;

q is one; and $R_{16}$ is defined hereinabove.

In this embodiment, the substituted spiro-hydantoin compound (II) is preferably the enantiomer represented by the substituted spiro-hydantoin compound (IIa).

In another different embodiment, the substituted spiro-hydantoin compound (II) is provided wherein:

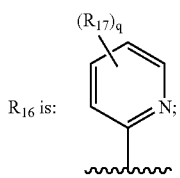

each $R_{17}$ is independently —$OR_{18}$, —$C(=O)R_{18}$, —$CO_2R_{18}$, and/or —$C(=O)NR_{18}R_{19}$; preferably at least one $R_{17}$ is —$CO_2R_{18}$; and more preferably at least one $R_{17}$ is —$CO_2H$;

$R_{18}$ and $R_{19}$ are independently hydrogen, alkyl, and/or substituted alkyl; and q is one.

In this embodiment, the substituted spiro-hydantoin compound (II) is preferably the enantiomer represented by the substituted spiro-hydantoin compound (IIa).

In a still different embodiment, the substituted spiro-hydantoin compound (II) is the substituted spiro-hydantoin compound (IIc) of formula:

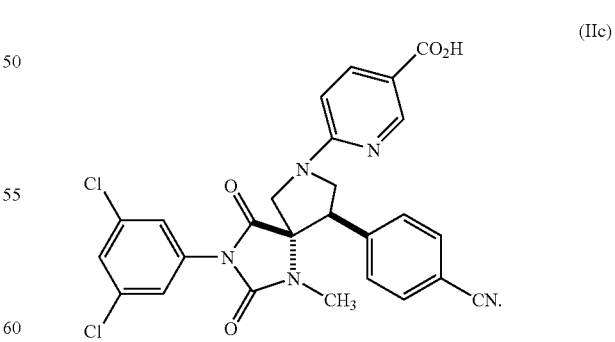

(IIc)

The substituted spiro-hydantoin compound (IIc) represents either enantiomer or a mixture thereof, including a racemic mixture of enantiomers. The enantiomers of the substituted spiro-hydantoin compound (IIc) are represented by substituted spiro-hydantoin compound (IId) of formula:

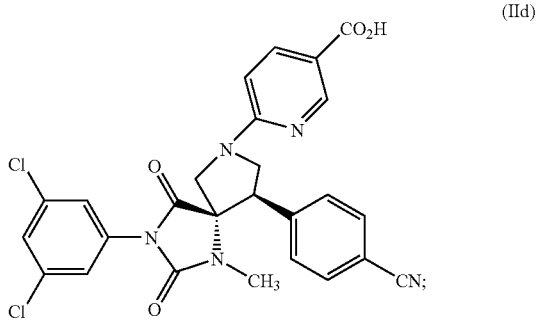

(IId)

and substituted spiro-hydantoin compound (IIe) of formula:

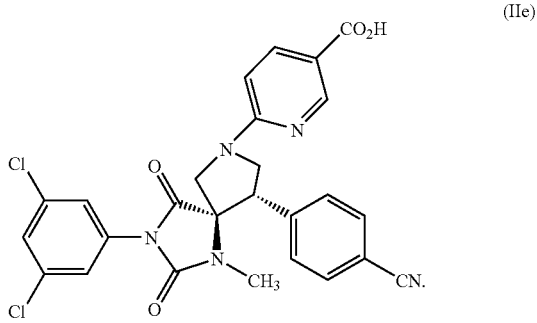

(IIe)

The substituted spiro-hydantoin compound (IId) is preferred.

The pyridyl-substituted spiro-hydantoins of formula II, particularly including crystalline and non-crystalline forms of compound (IId), demonstrate unexpectedly desirable pharmacological characteristics in comparison to known pyridyl substituted spiro-hydantoins. Such characteristics include improvements in the inhibition of the LFA-1:ICAM interaction. Other characteristics include diminished risk of undesirable drug-drug interactions and increased metabolic stability. For example, U.S. Patent Application Publication 2004/0009998 A1 discloses a compound having the formula:

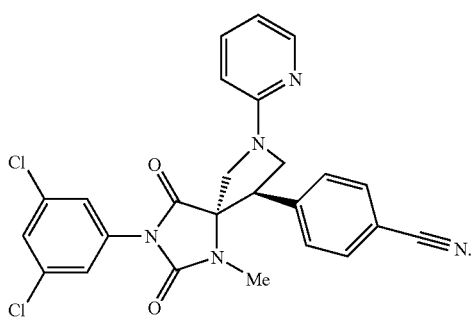

According to the CYP and liver microsomal assays described herein, infra, this compound, 4-[(5S*,9R *)-3-(3, 5-dichlorophenyl)-1-methyl-2,4-dioxo-7-pyridin-2-yl-1,3, 7-triazaspiro[4.4]non-9-yl]-benzonitrile, has a CYP 2C19 value of 0.11 micromolar and a rate of metabolism of 0.2 nmol/min/mg (human liver microsomes), respectively. In contrast, it has been discovered that a compound of formula II of the present invention, for example compound (IId), has a surprisingly high CYP 2C19 value of 38.2±2.22 micromolar indicating a much lower risk of drug-drug interactions and a rate of metabolism of 0.01±0.01 nmol/min/mg (human liver microsomes), indicating much higher metabolic stability.

The present invention also provides crystal forms of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid (substituted spiro-hydantoin compound (IId)). Various crystal forms of the substituted spiro-hydantoin compound (IId) were prepared and unit cell data and other properties for these examples are tabulated in Tables 1a and 1b.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High throughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, the crystallization technique, and the vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents. Examples of solvents for crystallization include, for example, mesitylene, cis-decalin, p-xylene, m-xylene, toluene, n-pentane, n-hexane, n-heptane, n-octane, tetrachloroethene, benzene, n-decane, n-dodecane, carbon disulfide, butylamine, diethyl ether, methyl tertiary-butyl ether, triethylamine, diisopropyl ether, dibutylether, 1,4-dioxane, tetrahydrofuran, chloroform, anisole, o-dichlorobenzene, ethyl formate, trichloroethene, methyl benzoate, iodobenzene, chlorobenzene, methyl ethanoate, dimethyl disulfide, 1,1-dichloroethane, fluorobenzene, ethyl phenyl ether, ethyl acetate, 1,2-dichloroethane, 1,2-dibromoethane, 1-iodobutane, 1,1,1-trichloroethane, propyl ethanoate, diethyl sulfide, dichloromethane, butyl ethanoate, methyl methanoate, bromoform, dibromomethane, m-cresol, 2-methoxyethanol, 1-butanol, propanoic acid, morpholine, 2-methyl-2-propanol, pentanoic acid, acetic acid, 2-propanol, 1-propanol, 1-octanol, ethanol, methyl ethyl ketone, 2,4-dimethylpyridine, acetophenone, 2,6-dimethylpyridine, 3-pentanone, 2-pentanone, 4-methylpyridine, acetone, cyclohexanone, 2-hexanone, cyclopentanone, 2-heptanone, 4-methyl-2-pentanone, 1,3-dimethyl-3,4,5,6-tetrahydro-2 (1H)-pyrimidinone, 1,3-dimethyl-2-imidazolidinone, pyrrolidinone, pyridine, N-methyl-2-pyrrolidone, N,N-dimethylformamide, N,N-dimethylacetamide, dimethylsulfoxide, benzonitrile, propanenitrile, acetonitrile, butanenitrile, nitromethane, nitrobenzene, aniline, benzyl alcohol, formic acid, ethylene glycol, methanol, diethylamine, diiodomethane, glycerol, water, formamide, N-methylacetamide, N-methylformamide, methyl acetate, isopropyl acetate, butyl acetate, t-butyl acetate, hexachloroacetone, N,N-dimethylpropionamide, t-butyl alcohol, hexamethylphosphoramide, 2-butanol, 2-nitroethanol, 2-fluoroethanol, 2,2,2-trifluoroethanol, 2-ethoxyethanol, neo-pentyl alcohol, t-pentyl alcohol, cyclohexanol, phenol, diethylene glycol, 1-, 2-, or 3-pentanol, 2-methyl-1-propanol, 2-butanol, diethylene glycol monomethyl ether, and methyl t-butyl ether.

In one method to prepare crystals, a compound is suspended and/or stirred in a suitable solvent to afford a slurry, which may be heated to promote dissolution. The term "slurry", as used herein, means a saturated solution of the compound, which may also contain an additional amount of the compound to afford a heterogeneous mixture of the compound and a solvent at a given temperature.

Seed crystals may be added to any crystallization mixture to promote crystallization. Seeding may be employed to control growth of a particular polymorph or to control the particle size distribution of the crystalline product. Accordingly, calculation of the amount of seeds needed depends on the size of the seed available and the desired size of an average product particle as described, for example, in "Programmed Cooling of Batch Crystallizers," J. W. Mullin and J. Nyvlt, *Chemical Engineering Science*, 1971, 26, 369–377. In general, seeds of small size are needed to control effectively the growth of crystals in the batch. Seed of small size may be generated by sieving, milling, or micronizing of large crystals, or by micro-crystallization of solutions. Care should be taken that milling or micronizing of crystals does not result in any change in crystallinity from the desired crystal form (i.e., change to amorphous or to another polymorph).

A cooled crystallization mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as solid state nuclear magnetic resonance, differential scanning calorimetry, x-ray powder diffraction, or the like, to assure formation of the preferred crystalline form of the product. The resulting crystalline form is typically produced in an amount of greater than about 70 weight % isolated yield, preferably greater than 90 weight % isolated yield, based on the weight of the compound originally employed in the crystallization procedure. The product may be comilled or passed through a mesh screen to delump the product, if necessary.

Crystalline forms may be prepared directly from the reaction medium of the final process for preparing the substituted spiro-hydantoin compound (IId). This may be achieved, for example, by employing in the final process step a solvent or a mixture of solvents from which the substituted spiro-hydantoin compound (IId) may be crystallized. Alternatively, crystalline forms may be obtained by distillation or solvent addition techniques. Preferably, such techniques may be carried out following the final process step for preparing the substituted spiro-hydantoin compound (IId). Suitable solvents for this purpose include, for example, the aforementioned nonpolar solvents and polar solvents, including protic polar solvents such as alcohols, and aprotic polar solvents such as ketones.

Samples of the crystalline forms may be provided with substantially pure phase homogeneity, indicating the presence of a dominant amount of a single polymorph and optionally minor amounts of one or more other polymorphs. The presence of more than one polymorph in a sample may be determined by techniques such as powder x-ray diffraction (XRPD) or solid state nuclear magnetic resonance spectroscopy. For example, the presence of extra peaks in the comparison of an experimentally measured XRPD pattern with a simulated XRPD pattern may indicate more than one polymorph in the sample. The simulated XRPD may be calculated from single crystal x-ray data. see Smith, D. K., "*A FORTRAN Program for Calculating X-Ray Powder Diffraction Patterns*," Lawrence Radiation Laboratory, Livermore, Calif., UCRL-7196 (April 1963). Preferably, the crystalline form has substantially pure phase homogeneity as indicated by less than 10%, preferably less than 5%, and more preferably less than 2% of the total peak area in the experimentally measured XRPD pattern arising from extra peaks that are absent from the simulated XRPD pattern. Most preferred is a crystalline form having substantially pure phase homogeneity with less than 1% of the total peak area in the experimentally measured XRPD pattern arising from the extra peaks that are absent from the simulated XRPD pattern.

In one aspect of this invention, a crystalline form of the substituted spiro-hydantoin compound (IId) is provided. This crystalline form is a neat crystal and is referred to herein as the "N-4" form, which includes the substituted spiro-hydantoin compound (IId) and/or zwitterion thereof.

In a different aspect of this invention, a different crystalline form of the substituted spiro-hydantoin compound (IId) is provided. This crystalline form is a hydrate crystal and is referred to herein as the "H-1" form, which includes the substituted spiro-hydantoin compound (IId) and/or zwitterion thereof, and water.

In another aspect of this invention, a crystalline solvate form of the substituted spiro-hydantoin compound (IId) is provided. This crystalline form is a chloroform solvate and is referred to herein as the "CHF-2" form, which includes the substituted spiro-hydantoin compound (IId) and chloroform.

In still another aspect of this invention, a crystalline salt form of the substituted spiro-hydantoin compound (IId) is provided. This crystalline form is a hydrochloric acid salt of the substituted spiro-hydantoin compound (IId), and is referred to herein as the "H3.5-1" form. The H3.5-1 form has a unit cell formed from one molecule of the substituted spiro-hydantoin compound (IId), one molecule of HCl, and 3.5 molecules of water.

In a further aspect of this invention, a different crystalline salt form of the substituted spiro-hydantoin compound (IId) is provided. This crystalline form is a hydrochloric acid salt of the substituted spiro-hydantoin compound (IId) and is referred to herein as the "H4-1" form. The H4-1 form has a unit cell formed from two molecules of the substituted spiro-hydantoin compound (IId), one molecule of HCl, and four molecules of water.

The unit cell parameters for several crystal forms of the spiro-hydantoin compound (IId) are tabulated in Tables 1a and 1b. The fractional atomic coordinates for the N-4 and the H-1 crystal forms are tabulated in Tables 2 and 3, respectively.

Unit Cell Parameters

| Form | a(Å) | b(Å) | c(Å) | α° | β° | γ° | V(Å$^3$) | T(°C.) |
|---|---|---|---|---|---|---|---|---|
| TABLE 1a ||||||||||
| N-4 | 10.02 | 14.67 | 16.78 | 90 | 90 | 90 | 2467.7 | 25 |
| H-1 | 8.017 | 9.574 | 16.94 | 79.11 | 84.20 | 83.48 | 1264.1 | 25 |
| CHF-2 | 11.91 | 12.21 | 20.59 | 90 | 90 | 90 | 2994.1 | −50 |
| H3.5-1 | 7.597 | 10.77 | 19.23 | 79.91 | 88.60 | 74.78 | 1494.3 | 25 |
| H4-1 | 7.564 | 17.27 | 20.92 | 90 | 95.35 | 90 | 2720.1 | −50 |

TABLE 1b

| Form | Z | V$_m$ | SG | D$_{calc}$ (g/cm$^3$) | MP (° C.) |
|---|---|---|---|---|---|
| N-4 | 4 | 617 | P2$_1$2$_1$2$_1$ | 1.444 | 250(melt) |
| H-1 | 2 | 632 | P1 | 1.425 | 100(desolvate) 205–215(melt) |
| CHF-2 | 1 | 749 | P2$_1$2$_1$2$_1$ | 1.455 | — |
| H3.5-1 | 2 | 747 | P$_1$ | 1.433 | — |
| H4-1 | 1 | 680 | P2$_1$ | 1.487 | — |

Notes
for Table 1:
T is the temperature of the crystal.
Z is the number of molecules of the substituted spiro-hydantoin compound (IId) in each unit cell.
V$_m$ is the molar volume.
SG is the crystallographic space group.
D$_{calc}$ is the calculated density.
MP is the melting point or temperature of desolvation).

TABLE 2

Positional Parameters for 6-[(5S,9R)-9-(4-cyanophenyl)-3-(3,5-dichlorophenyl)-1-methyl-2,4-dioxo-1,3,7-triazaspiro[4.4]non-7-yl]nicotinic acid form N-4 at +25° C.

| atom | X | Y | Z |
|---|---|---|---|
| CL1 | −0.1864 | 0.0025 | 0.0616 |
| CL2 | 0.1131 | 0.2753 | −0.0505 |
| O3 | 1.0323 | 0.3040 | 0.4946 |
| C4 | 0.5098 | 0.0546 | 0.3560 |
| N5 | 0.7268 | 0.1594 | 0.4043 |
| O6 | 0.3529 | 0.1447 | 0.2180 |
| O7 | 0.3185 | −0.1108 | 0.0632 |
| O8 | 1.1765 | 0.2645 | 0.3997 |
| C9 | 0.0292 | −0.0782 | 0.3573 |
| N10 | 0.4572 | −0.0758 | 0.1699 |
| C11 | 0.0975 | 0.1768 | 0.0061 |
| C12 | 0.3002 | −0.0421 | 0.3313 |
| N13 | 0.6225 | 0.0766 | 0.3055 |
| C14 | 0.8342 | 0.2047 | 0.4334 |
| N15 | 0.3078 | 0.0270 | 0.1295 |
| C16 | −0.0333 | 0.0565 | 0.0558 |
| C17 | 0.4443 | −0.0221 | 0.3121 |
| C18 | 0.4720 | −0.0012 | 0.2244 |
| C19 | 0.9595 | 0.1776 | 0.3145 |
| C20 | 0.6163 | 0.0398 | 0.2250 |
| C21 | 0.1948 | 0.0663 | 0.0884 |
| C22 | −0.0246 | 0.1338 | 0.0090 |
| C23 | 0.7320 | 0.1234 | 0.3302 |
| C24 | 0.2257 | 0.0150 | 0.3822 |
| C25 | 0.8517 | 0.1319 | 0.2839 |
| C26 | 0.0749 | 0.0204 | 0.0946 |
| C27 | 0.5321 | −0.1619 | 0.1705 |
| C28 | 0.9522 | 0.2157 | 0.3911 |
| C29 | 0.3702 | 0.0677 | 0.1920 |
| C30 | 0.0885 | −0.0065 | 0.3964 |
| C31 | 0.2374 | −0.1169 | 0.2965 |
| C32 | 1.0660 | 0.2646 | 0.4280 |
| N33 | −0.2277 | −0.1067 | 0.3698 |
| C34 | 0.2107 | 0.1447 | 0.0456 |
| C35 | 0.1014 | −0.1341 | 0.3097 |

TABLE 2-continued

Positional Parameters for 6-[(5S,9R)-9-(4-cyanophenyl)-3,5-dichlorophenyl)-1-methyl-2,4-dioxo-1,3,7-triazaspiro[4.4]non-7-yl]nicotinic acid form N-4 at +25° C.

| atom | X | Y | Z |
|---|---|---|---|
| C36 | −0.1144 | −0.0943 | 0.3661 |
| C37 | 0.3587 | −0.0619 | 0.1158 |

TABLE 3

Positional Parameters for 6-[(5S,9R)-9-(4-cyanophenyl)-3-(3,5-dichlorophenyl)-1-methyl-2,4-dioxo-1,3,7-triazaspiro[4.4]non-7-yl]nicotinic acid form H-1 at +25° C.

| atom | X | Y | Z |
|---|---|---|---|
| CL1 | 0.9090 | 0.5577 | −0.1122 |
| CL2 | 1.1071 | 0.1391 | 0.1242 |
| O3 | 0.6676 | 0.6917 | 0.1901 |
| O4 | 0.4412 | 0.2825 | 0.1768 |
| O5 | 0.6512 | 1.0411 | 0.5854 |
| O6 | 0.5591 | 1.2486 | 0.5144 |
| N7 | 0.5840 | 0.4846 | 0.1656 |
| N8 | 0.3773 | 0.7996 | 0.3146 |
| N9 | 0.4801 | 0.8117 | 0.4350 |
| N10 | 0.3426 | 0.4696 | 0.2423 |
| N11 | 0.1753 | 0.8772 | −0.2022 |
| C12 | 0.5662 | 0.6035 | 0.1982 |
| C13 | 0.3907 | 0.6104 | 0.2437 |
| C14 | 0.7261 | 0.4411 | 0.1141 |
| C15 | 0.2575 | 0.7586 | 0.1149 |
| C16 | 0.2646 | 0.7357 | 0.2055 |
| C17 | 0.4244 | 0.8815 | 0.3647 |
| C18 | 0.5183 | 1.0370 | 0.4688 |
| C19 | 0.3144 | 0.8648 | 0.2373 |
| C20 | 0.5293 | 0.8910 | 0.4852 |
| C21 | 0.8814 | 0.4707 | −0.0128 |
| C22 | 0.4525 | 0.3961 | 0.1936 |
| C23 | 0.9686 | 0.2836 | 0.0911 |
| C24 | 0.8347 | 0.3269 | 0.1434 |
| C25 | 0.2172 | 0.8168 | −0.0496 |
| C26 | 0.4108 | 1.0293 | 0.3439 |
| C27 | 0.4589 | 1.1072 | 0.3972 |
| C28 | 0.7468 | 0.5163 | 0.0355 |
| C29 | 0.0893 | 0.7659 | 0.0033 |
| C30 | 0.5754 | 1.1209 | 0.5242 |
| C31 | 0.3840 | 0.8134 | 0.0600 |
| C32 | 0.4008 | 0.6446 | 0.3292 |
| C33 | 0.1076 | 0.7354 | 0.0865 |
| C34 | 0.9931 | 0.3547 | 0.0130 |
| C35 | 0.1944 | 0.8488 | −0.1362 |
| C36 | 0.1807 | 0.4188 | 0.2741 |
| C37 | 0.3673 | 0.8425 | −0.0228 |
| CL38 | 0.7159 | 0.0119 | 1.0809 |
| CL39 | 0.3918 | 0.4651 | 0.9027 |
| O40 | 0.7674 | 0.1908 | 0.6866 |
| O41 | 0.8037 | −0.1413 | 0.2773 |
| O42 | 0.9052 | −0.3400 | 0.3564 |
| O43 | 1.1579 | 0.2044 | 0.8636 |
| C44 | 1.0987 | 0.2073 | 0.7999 |
| C45 | 0.9396 | −0.1167 | 0.3902 |
| C46 | 0.9093 | 0.0297 | 0.3729 |
| C47 | 1.0239 | 0.0543 | 0.4883 |
| N48 | 0.9266 | 0.2038 | 0.7904 |

TABLE 3-continued

Positional Parameters for 6-[(5S,9R)-9-(4-cyanophenyl)-3-(3,5-dichlorophenyl)-1-methyl-2,4-dioxo-1,3,7-triazaspiro[4.4]non-7-yl]nicotinic acid form H-1 at +25° C.

| atom | X | Y | Z |
|---|---|---|---|
| N49 | 1.1823 | 0.2156 | 0.7257 |
| N50 | 1.0556 | 0.1439 | 0.5384 |
| N51 | 0.9478 | 0.1175 | 0.4206 |
| C52 | 1.0672 | 0.3475 | 0.5958 |
| C53 | 1.0703 | 0.2123 | 0.6638 |
| C54 | 0.7962 | 0.2085 | 0.8551 |
| C55 | 1.1150 | 0.0857 | 0.6181 |
| C56 | 0.9991 | 0.2961 | 0.5253 |
| C57 | 0.9026 | 0.2004 | 0.7121 |
| C58 | 0.8144 | 0.1119 | 0.9262 |
| C59 | 1.0692 | −0.0895 | 0.5071 |
| C60 | 0.6644 | 0.3154 | 0.8465 |
| C61 | 0.8824 | −0.2118 | 0.3411 |
| C62 | 0.9705 | 0.4778 | 0.6248 |
| C63 | 1.0228 | −0.1782 | 0.4592 |
| C64 | 0.5600 | 0.2310 | 0.9835 |
| C65 | 0.5491 | 0.3242 | 0.9121 |
| C66 | 0.7989 | 0.5113 | 0.6217 |
| C67 | 1.0653 | 0.5587 | 0.6608 |
| C68 | 0.6938 | 0.1273 | 0.9899 |
| C69 | 0.7139 | 0.6211 | 0.6592 |
| C70 | 0.8094 | 0.6982 | 0.6970 |
| C71 | 1.3641 | 0.2118 | 0.7152 |
| C72 | 0.9814 | 0.6708 | 0.6972 |
| C73 | 0.7229 | 0.8038 | 0.7418 |
| N74 | 0.6535 | 0.8812 | 0.7796 |
| O75 | 0.7518 | 0.4008 | 0.3383 |
| O76 | 0.4176 | 0.5330 | 0.5345 |

Peaks found in the powder x-ray diffraction patterns of various crystalline forms are listed in Tables 4–8. The tables also list the d-spacing for each 2θ value, calculated using Bragg's Law.

TABLE 4

N-4

| 2θ(°) | 10.3 | 13.1 | 21.0 | 22.0 | 22.8 | 29.3 |
|---|---|---|---|---|---|---|
| d(Å) | 8.61 | 6.73 | 4.24 | 4.04 | 3.90 | 3.04 |

TABLE 5

H-1

| 2θ(°) | 5.34 | 9.45 | 11.15 | 12.8 | 15.5 | 23.5 | 25.0 |
|---|---|---|---|---|---|---|---|
| d(Å) | 16.5 | 9.35 | 7.93 | 6.94 | 5.71 | 3.79 | 3.57 |

TABLE 6

CHF-2

| 2θ(°) | 8.59 | 13.5 | 14.5 | 14.9 | 15.1 | 18.7 | 24.6 |
|---|---|---|---|---|---|---|---|
| d(Å) | 10.3 | 6.56 | 6.10 | 5.94 | 5.85 | 4.74 | 3.61 |

TABLE 7

H3.5-1

| 2θ(°) | 4.66 | 8.64 | 9.10 | 9.35 | 10.5 | 16.7 | 21.1 | 21.4 | 26.7 | 28.3 |
|---|---|---|---|---|---|---|---|---|---|---|
| d(Å) | 18.9 | 10.2 | 9.71 | 9.45 | 8.41 | 5.29 | 4.20 | 4.15 | 3.33 | 3.15 |

TABLE 8

H4-1

| 2θ(°) | 4.25 | 6.65 | 10.2 | 16.0 | 16.5 | 21.7 | 26.4 | 29.9 |
|---|---|---|---|---|---|---|---|---|
| d(Å) | 20.8 | 13.3 | 8.62 | 5.55 | 5.38 | 4.10 | 3.37 | 2.99 |

Methods of Preparation

The substituted spiro-hydantoin compounds of formula II may be prepared by the exemplary processes described in the following reaction Schemes A–D. Exemplary reagents and procedures of these reactions appear hereinafter. Starting materials are commercially available or can be readily prepared by one of ordinary skill in the art. The solvents, temperatures, pressures, starting materials having the desired groups, and other reaction conditions, may be readily selected as appropriate by one of ordinary skill in the art.

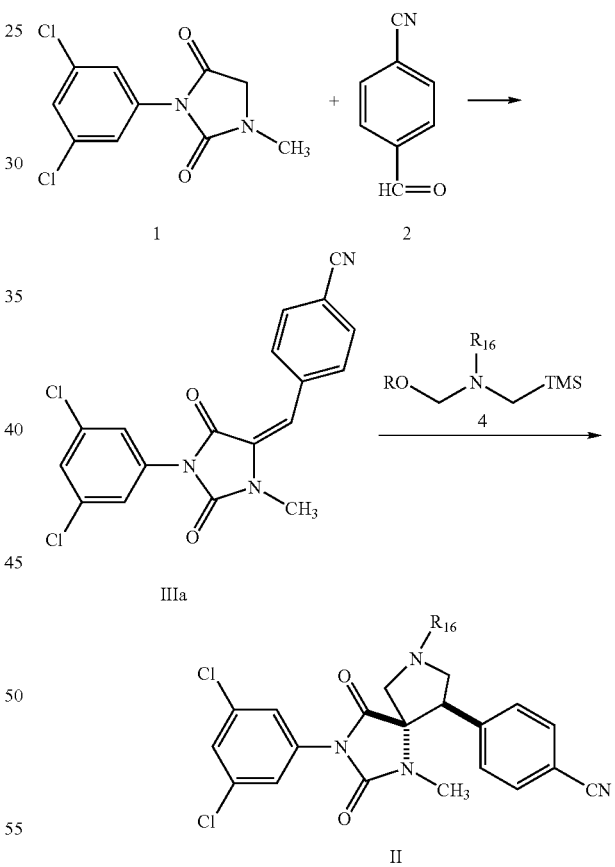

Hydantoins 1 can be submitted to a Knoevenagel condensation with an aromatic aldehyde 2 under classical conditions (e.g., sodium acetate in refluxing acetic anhydride) to obtain alkene compound (IIIa), which is reacted with amine 4 under acidic catalysis (such as trifluoroacetic acid) to yield substituted spiro-hydantoin compound (II).

SCHEME B

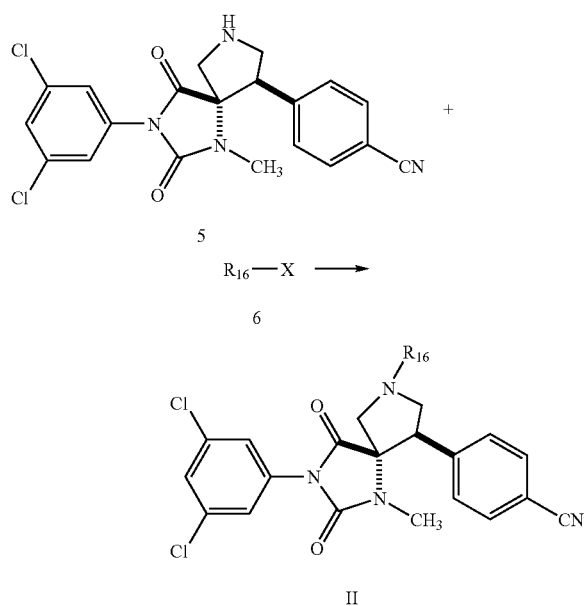

Spiro-hydantoin compound 5 can be alkylated by reaction with an alkyl halide 6, in a solvent such as acetonitrile or acetone at temperatures ranging from room temperature to reflux, to yield the substituted spiro-hydantoin compound (II). Processes to prepare the spiro-hydantoin compound 5 and substituted spiro-hydantoin compounds (II) are disclosed in U.S. Patent Application Publication 2004/0009998A1.

SCHEME C

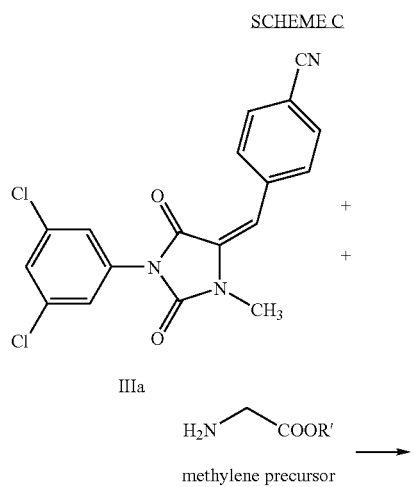

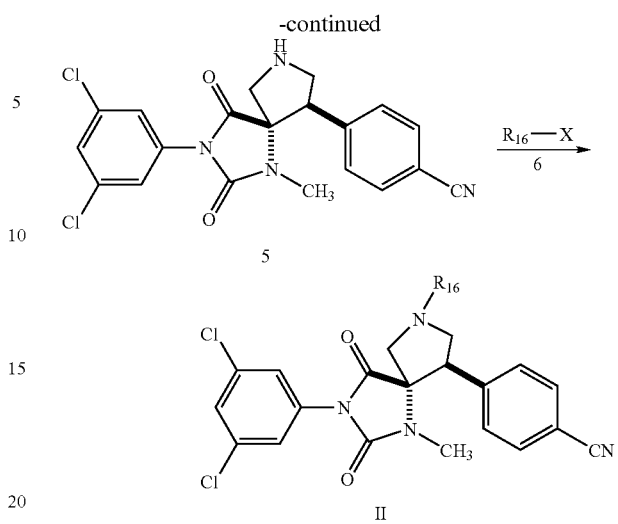

The spiro-hydantoin compound 5 can be prepared by reacting the alkene compound (IIIa) with glycine or a glycine ester 7, and a methylene precursor compound in the presence of a polar solvent. The methylene source serves as a source of a methylene group. The methylene precursor compound may provide the methylene group directly, such as through decomposition of the methylene precursor compound, or indirectly through the formation of an intermediate compound that subsequently forms the methylene group. Examples of methylene precursor compounds include, for example, formaldehyde, dimethoxymethane, trioxane, paraformaldehyde, and hexamethylenetetramine. Formaldehyde may be provided as a gas, which can be bubbled into the reaction mixture, or as an aqueous formaldehyde solution. Suitable glycine esters include glycine alkyl esters such as glycine methyl ester and glycine ethyl ester. Preferred is glycine.

Alternatively, the methylene precursor compound and the glycine or glycine ester compound may be provided as a condensation product of the methylene precursor compound and the glycine or glycine ester. Examples of suitable condensation products of the methylene precursor compound include:

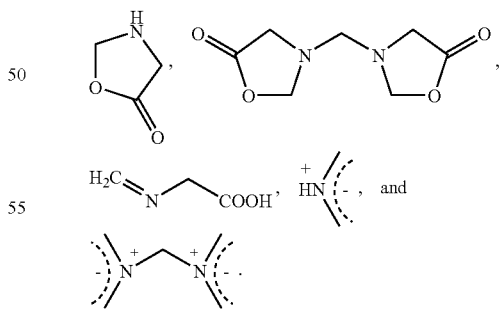

The alkene compound (IIIa) may be contacted with the methylene precursor compound, and the glycine or glycine ester by admixing these ingredients in any order, such as, for example, combining the alkene compound (IIIa) with glycine to form a mixture, and then adding to the mixture the methylene precursor compound to the mixture. The alkene compound (IIIa), the methylene precursor compound, and the glycine or glycine ester may be combined prior to reaction, or alternatively, one or more of these ingredients may be gradually added to the reaction mixture during the course of the reaction.

The reaction is conducted in the presence of a polar solvent. As used herein, "polar solvent" refers to a solvent having a dielectric constant of at least 15. Preferably, the polar solvent has a dielectric constant of at least 30. Suitable polar solvents include, for example, acetone, acetonitrile, 1-butanol, 2-butanol, N,N-dimethylacetamide, dimethylformamide, isobutyl alcohol, methanol, 2-methoxyethanol, methylethylketone, 1-methyl-2-pyrrolidinone, 1-propanol, 2-propanol, tetramethyl urea, or mixtures thereof. Preferred polar solvents include acetonitrile, N,N-dimethylacetamide, dimethylformamide, methanol, methylethylketone, 1-methyl-2-pyrrolidinone, or mixtures thereof. A more preferred polar solvent is 1-methyl-2-pyrrolidinone. Typically, the reaction may be conducted in a solvent mixture comprising the polar solvent and nonpolar solvent. As used herein, "nonpolar solvent" refers to refers to a solvent having a dielectric constant of less than 15. Preferably, the nonpolar solvent has a dielectric constant of less than 10, and more preferably, less than 5. Suitable nonpolar solvents include, for example, benzene; toluene; or xylene (ortho, meta, para, or a mixture thereof); alkanes such as hexane, heptane, and cyclohexane; and chlorinated solvents such as carbon tetrachloride and chloroform. Mixtures of nonpolar solvent may be employed. Examples of suitable polar/nonpolar solvent mixtures include ratios of polar solvent to nonpolar solvent in the range of about 95:5 to about 5:95, preferably in the range of from about 85:15 to about 45:55, and more preferably in the range of from about 75:25 to about 55:45, based on weight. A preferred polar/nonpolar solvent mixture is 1-methyl-2-pyrrolidinone and toluene in a ratio in the range of from about 63:33, based on weight.

Suitable reaction temperatures for this reaction include temperatures in the range of from about 100° C. to about 160° C. The reaction may be conducted in the presence of synthesis adjuvants such as water or metal salts with or without ligands. Preferably, the amount of water in the reaction mixture is minimized. For example, the reaction may be conducted with a reaction mixture that includes less than 3 weight %, preferably less than 2 weight %, and more preferably, less than 1 weight %, based on the weight of the reaction mixture. Techniques to minimize the level of water in the reaction mixture are known in the art, and include removing water from reagents and solvents prior conducting the reaction. The amount of water in the reaction mixture may be determined by Karl Fischer titration. The extent of reaction may be monitored by a suitable technique such as high pressure liquid chromatography (HPLC) or nuclear magnetic resonance detection.

The process Scheme C affords the spiro-hydantoin compound 5 and optionally aminal of the spiro-hydantoin compound 5. An aminal of spiro-hydantoin compound 5 has the structure:

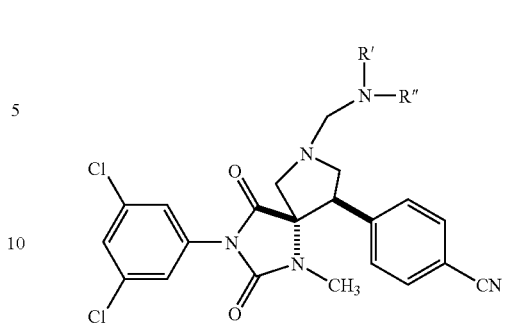

wherein R' and R" represent substituent groups and optionally R' and R" may be joined to form a ring. In one embodiment, the aminal is an aminal dimer of the spiro-hydantoin compound 5 and is formed between two molecules of the spiro-hydantoin compound 5 that are linked together by a methylene bridge between the two ring amines. One example of an aminal dimer of the spiro-hydantoin compound 5 is

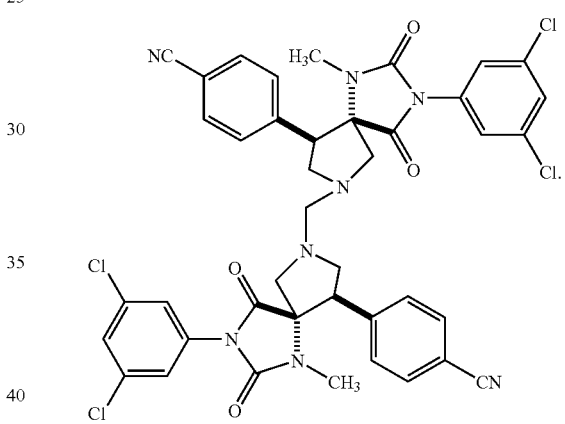

After completion of the reaction, the reaction mixture may contain a mixture of the spiro-hydantoin compound 5 and one or more aminals of the spiro-hydantoin compound 5. The aminal may be cleaved by acidifying the reaction mixture with the addition of an acid such as hydrochloric acid, hydrobromic acid, sulfuric acid, or methanesulfonic acid to afford the spiro-hydantoin compound 5 in greater yield. Another method to cleave the aminal dimer is addition of bisulfite salt. Alternatively, the aminal may be cleaved by treatment with an amine or diamine, for example, ethylene diamine, N-methyl diamine, or propylenediamine. A combination of the aforementioned methods may be employed to cleaved the aminal. The spiro-hydantoin compound 5 may be obtained by cooling the reaction mixture to a temperature below about 30° C., and filtering the spiro-hydantoin compound 5 from the reaction mixture. The resulting spiro-hydantoin compound 5 may be obtained as a salt, for example, as a hydrochloric acid salt; or worked up with an organic solvent and aqueous workup to afford spiro-hydantoin compound 5.

The process of Scheme C may optionally include a step for separating the enantiomers of spiro-hydantoin compound 5 to provide the individual enantiomers. These enantiomers are represented by spiro-hydantoin compound 5a

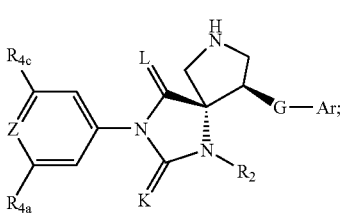

(5a)

and spiro-hydantoin compound 5b:

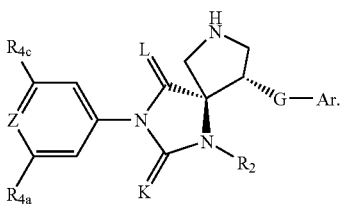

(5b)

The enantiomers of the spiro-hydantoin compound 5 may be resolved from a racemic mixture by various method known in the art, such as, for example, classical resolution, separation by chiral chromatography such as with a simulating moving bed or HPLC, or enzymatic resolution. In one non-limiting embodiment, the enantiomers of spiro-hydantoin compound 5 are resolved by contacting the racemic mixture of spiro-hydantoin compound 5 with an enantiomeric acid. Examples of enantiomeric acids include tartaric acid; O-substituted tartaric acid such as (+)-di-p-toluoyl-D-tartaric acid, (+)-di-p-benzoyl-D-tartaric acid, (+)-di-p-o-toluoyl-D-tartaric acid, enantiomers of these acids, or a mixtures thereof. Preferred is (+)-di-p-toluoyl-D-tartaric acid. In this embodiment, the racemic mixture of spiro-hydantoin compound 5 is provided as a mixture in a suitable solvent, such as methyl tertiary butyl ether, methylene chloride, 2-butanone, methyl isobutylketone, or mixture thereof; and contacted with the enantiomeric acid. The resulting mixture is seeded and cooled to allow crystallization of the salt formed by an enantiomer of spiro-hydantoin compound 5 and the corresponding enantiomeric acid. The enantiomer 5a or the enantiomer 5b may be employed as a reagent in a subsequent reaction, such as the preparation of a specific enantiomer of the substituted spiro-hydantoin compound (I) or (II).

The present invention also provides a process for preparing a substituted spiro-hydantoin compound (I),

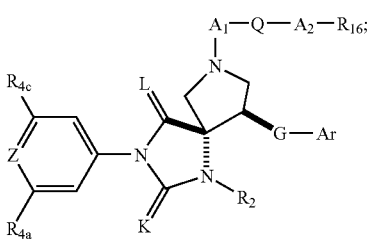

(I)

such as the substituted spiro-hydantoin compound (II) or the substituted spiro-hydantoin compound (IId).

SCHEME D

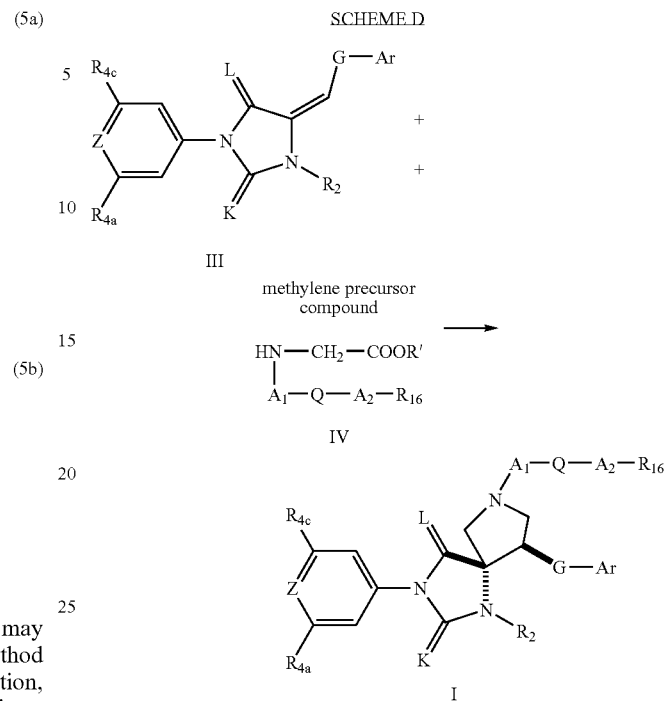

This process of this invention comprises:
a) contacting alkene compound (III)
b) methylene precursor compound; and
c) N-substituted glycine compound (IV) to afford said substituted spiro-hydantoin compound (I), or pharmaceutically-acceptable salts, solvates, or prodrugs thereof;

wherein:

L and K are independently O or S;

Z is N or $CR_{4b}$;

Ar is aryl, substituted aryl, heteroaryl, or substituted heteroaryl;

G is a bond, —O—, —S—, —$NR_1$, $C_{1-3}$alkylene, $C_{1-3}$substituted alkylene, bivalent alkoxy, thioalkyl, aminoalkyl, sulfonyl, sulfonamidyl, acyl, or alkoxycarbonyl;

$A_1$ is a bond, $C_{1-2}$alkylene, or $C_{2-3}$alkenylene;

$A_2$ is a bond, $C_{1-3}$alkylene, $C_{2-3}$alkenylene, —$C_{1-4}$alkylene-$NR_{16}$—, —$C_{1-4}$alkylene-$NR_{16}$C(=O)—, —$C_{1-4}$alkylene-S—, —$C_{1-4}$alkylene-$SO_2$—, or —$C_{1-4}$alkylene-O—, wherein the $A_2$ alkylene groups are branched or straight chain, and optionally substituted alkylene;

Q is a bond, —C(=O)—, —C(=O)$NR_{16}$—, —C(=S)$NR_{16}$—, —$SO_2$—, —$SO_2NR_{16}$—, —$CO_2$—, or —$NR_{16}CO_2$—;

$R_1$ is hydrogen, alkyl, or substituted alkyl;

$R_2$ is hydrogen, alkyl, substituted alkyl, —$OR_{12}$, —$NR_{12}R_{13}$, —C(=O)$R_{12}$, —$CO_2R_{12}$, —C(=O)$NR_{12}R_{13}$, —$NR_{12}$C(=O)$R_{13}$, —$NR_{12}$C(=O)$OR_{13}$, —S(O)$_pR_{13a}$, —$NR_{12}SO_2R_{13a}$, —$SO_2NR_{12}R_{13}$, cycloalkyl, substituted cycloalkyl, heterocyclo, substituted heterocyclo, aryl, substituted aryl, heteroaryl, or substituted heteroaryl;

$R_{4a}$, $R_{4b}$, and $R_{4c}$ are independently hydrogen, halogen, alkyl, substituted alkyl, alkenyl, substituted alkenyl, nitro, cyano, —$SR_{14}$, —$OR_{14}$, —$NR_{14}R_{15}$, —$NR_{14}$C(=O)$R_{15}$, —$CO_2R_{14}$, —C(=O)$R_{14}$, —C(=O)$NR_{14}R_{15}$, aryl, substituted aryl, heterocyclo, substituted heterocyclo, cycloalkyl, substituted cycloalkyl, heteroaryl, and/or substituted heteroaryl;

$R_{12}$, $R_{13}$, $R_{14}$, and $R_{15}$ are independently hydrogen, alkyl, substituted alkyl, cycloalkyl, substituted cycloalkyl, aryl, substituted aryl, heteroaryl, substituted heteroaryl, heterocyclo, and/or substituted heterocyclo; or (ii) $R_{12}$ is taken together with $R_{13}$, and/or $R_{14}$ is taken together with $R_{15}$ to form a heteroaryl or heterocyclo ring;

$R_{13a}$ is alkyl, substituted alkyl, cycloalkyl, aryl, substituted aryl, heteroaryl, substituted heteroaryl, heterocyclo, or substituted heterocyclo;

$R_{16}$ is hydrogen, alkyl, substituted alkyl, alkenyl, substituted alkenyl, aryl, substituted aryl, heteroaryl, substituted heteroaryl, heterocyclo, substituted heterocyclo, cycloalkyl, or substituted cycloalkyl, provided that $R_{16}$ is not hydrogen when $A_1$, Q, and $A_2$ are each bonds;

R' is hydrogen, alkyl, substituted alkyl, alkenyl, substituted alkenyl, aryl, substituted aryl, heteroaryl, substituted heteroaryl, heterocyclo, substituted heterocyclo, cycloalkyl, or substituted cycloalkyl; and p is 1 or 2.

As used herein, the substituted spiro-hydantoin compound (I) represents either enantiomer of the substituted spiro-hydantoin compound (I) or a mixture thereof in any ratio of enantiomers, including a racemic mixture of the enantiomers. The enantiomers of the substituted spiro-hydantoin compound (I) are represented by substituted spiro-hydantoin compound (Ia) of formula:

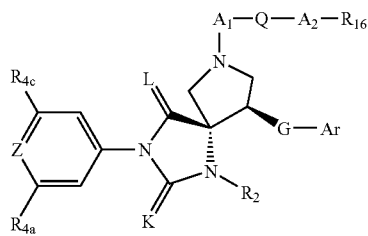

and substituted spiro-hydantoin compound (Ib) of formula:

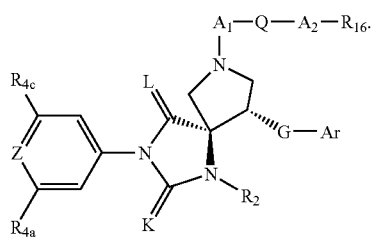

In the process of the invention, the alkene compound (III) is contacted with at least one methylene precursor compound, and N-substituted glycine compound (IV). The methylene precursor compound serves as a source of a methylene group. The methylene precursor compound may provide the methylene group directly, such as through decomposition of the methylene precursor compound, or indirectly through the formation of an intermediate compound that subsequently forms the methylene group. Examples of methylene precursor compounds include, for example, formaldehyde, dimethoxymethane, trioxane, paraformaldehyde, and hexamethylenetetramine. Formaldehyde may be provided as a gas, which can be bubbled into the reaction mixture, or as an aqueous formaldehyde solution. A preferred methylene precursor compound is hexamethylenetetramine.

The N-substituted glycine compound (IV) is N-substituted glycine or N-substituted glycine ester, and is represented by formula IV

wherein:

$A_1$ is a bond, $C_{1-2}$alkylene, or $C_{2-3}$alkenylene;

$A_2$ is a bond, $C_{1-3}$alkylene, $C_{2-3}$alkenylene, —$C_{1-4}$alkylene-$NR_{16}$—, —$C_{1-4}$alkylene-$NR_{16}$C(=O)—, —$C_{1-4}$alkylene-S—, —$C_{1-4}$alkylene-$SO_2$—, or —$C_{1-4}$alkylene-O—, wherein the $A_2$ alkylene groups are branched or straight chain, and optionally substituted alkylene;

Q is a bond, —C(=O)—, —C(=O)$NR_{16}$—, —C(=S)$NR_{16}$—, —$SO_2$—, —$SO_2NR_{16}$—, —$CO_2$—, or —$NR_{16}CO_2$—;

R' is hydrogen, alkyl, substituted alkyl, alkenyl, substituted alkenyl, aryl, substituted aryl, heteroaryl, substituted heteroaryl, heterocyclo, substituted heterocyclo, cycloalkyl, or substituted cycloalkyl; and $R_{16}$ is hydrogen, alkyl, substituted alkyl, alkenyl, substituted alkenyl, aryl, substituted aryl, heteroaryl, substituted heteroaryl, heterocyclo, substituted heterocyclo, cycloalkyl, or substituted cycloalkyl, provided that $R_{16}$ is not hydrogen when $A_1$, Q, and $A_2$ are each bonds.

The alkene compound (III) may be contacted with the methylene precursor compound, and the N-substituted glycine compound (IV) by admixing these ingredients in any order, such as, for example, combining the alkene compound (III) with N-substituted glycine compound (IV) to form a mixture, and then adding to the methylene precursor compound to the mixture. The alkene compound (III), the methylene precursor compound, and the N-substituted glycine compound may be combined prior to reaction, or alternatively, one or more of these ingredients may be gradually added to the reaction mixture during the course of the reaction.

The reaction is typically conducted in solvent, for example one or more nonpolar solvents, one or more polar solvents, or mixtures thereof. Preferably, the reaction is conducted in the presence of at least one polar solvent and optionally, at least one nonpolar solvent. Mixtures of nonpolar solvent may be employed. Examples of suitable polar/nonpolar solvent mixtures include ratios of polar solvent to nonpolar solvent in the range of about 95:5 to about 5:95, preferably in the range of from about 85:15 to about 45:55, and more preferably in the range of from about 75:25 to about 55:45, based on weight. A preferred polar/nonpolar solvent mixture is 1-methyl-2-pyrrolidinone and toluene in a ratio in the range of about 63:33, based on weight.

Suitable reaction temperatures for this reaction include temperatures in the range of from about 100° C. to about 160° C. The reaction may be conducted in the presence of synthesis adjuvants such as water or metal salts with or without ligands. Preferably, the amount of water in the reaction mixture is minimized. For example, the reaction may be conducted with a reaction mixture that includes less than 3 weight %, preferably less than 2 weight %, and more preferably, less than 1 weight %, based on the weight of the reaction mixture. Techniques to minimize the level of water in the reaction mixture are known in the art, and include removing water from reagents and solvents prior conducting the reaction. The amount of water in the reaction mixture may be determined by Karl Fischer titration. The extent of reaction may be monitored by a suitable technique such as high pressure liquid chromatography (HPLC) or nuclear magnetic resonance detection.

The process of the invention may optionally include a step for separating the substituted spiro-hydantoin compound (I) to provide the individual enantiomers represented by formulae Ia and Ib. Suitable techniques for resolving enantiomers are disclosed hereinabove.

In one embodiment, the process of the invention is directed towards the preparation of the substituted spiro-hydantoin compound (I) wherein Z is $CR_{4b}$; K is O; L is O; and Ar, G, $R_2$, $R_{4a}$, $R_{4b}$, $R_{4c}$, $A_1$, $A_2$, Q, and $R_{16}$ are defined hereinabove. The substituted spiro-hydantoin compound (I) of this embodiment has the formula Ic:

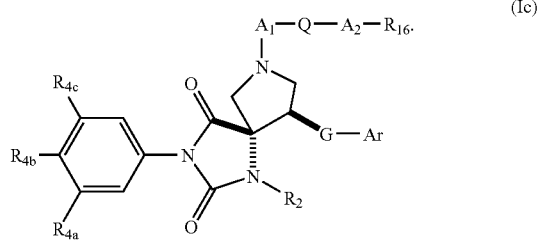

The process may be employed to prepared either enantiomer of the substituted spiro-hydantoin compound (Ic), represented by the substituted spiro-hydantoin compound (Id):

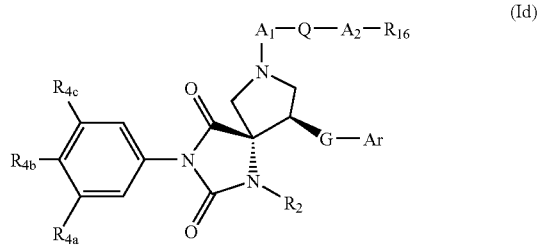

and the substituted spiro-hydantoin compound (Ie):

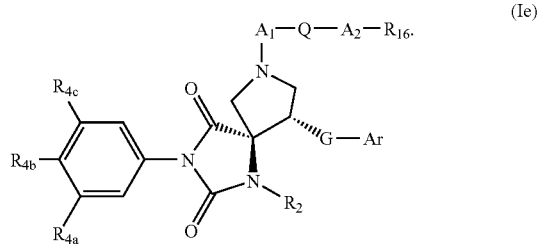

The substituted spiro-hydantoin compound (Id) is preferred.

In another different embodiment, the process of the invention is directed towards the preparation of the substituted spiro-hydantoin compound (I) wherein: Z is $CR_{4b}$; K is O; L is O; Ar is aryl or substituted aryl; G is a bond, $C_{1-3}$alkylene, or $C_{1-3}$ substituted alkylene; $R_2$ is alkyl or substituted alkyl; and $R_{4a}$, $R_{4c}$, $A_1$, $A_2$, Q, and $R_{16}$ are defined hereinabove.

In a still different embodiment, the process of the invention is directed towards the preparation of the substituted spiro-hydantoin compound (I) wherein: Z is $Ca_{4b}$; $R_{4b}$ is H or lower alkyl; K is O; L is O; Ar is substituted aryl; G is a bond or methylene; $R_2$ is alkyl or substituted alkyl; $R_{4a}$ is F, Cl, or Br; $R_{4c}$ is F, Cl, or Br; $A_1$ is alkylene; $A_2$ is a bond; Q is a bond and $R_{16}$ is a heterocyclo or substituted heterocyclo.

In a preferred embodiment, the process of this invention is directed towards the preparation of a substituted spiro-hydantoin compound having the formula Ii:

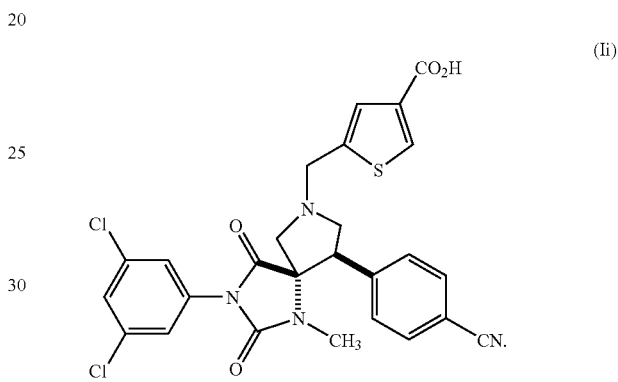

In this embodiment, the substituted spiro-hydantoin compound (Ii) is prepared by:

a) reacting the methylene precursor compound, and the N-substituted glycine compound (IVa) having the formula:

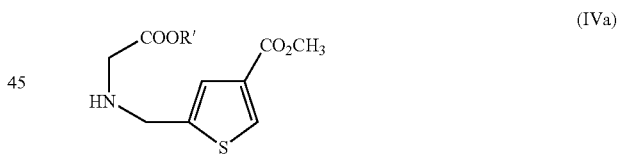

with alkene compound (IIIa) of formula

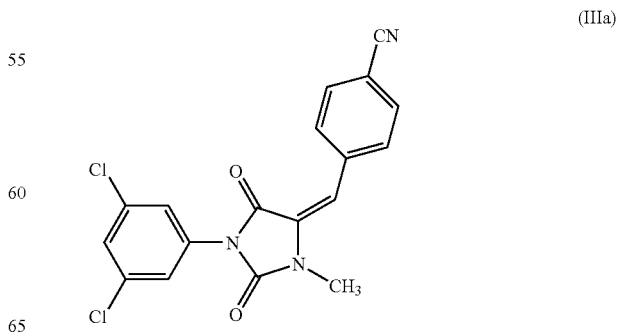

to afford substituted spiro-hydantoin compound (If) of formula

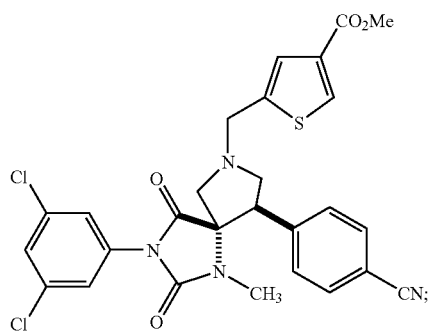
(If)

b) hydrolyzing the methyl ester of the substituted spiro-hydantoin compound (If) to afford the substituted spiro-hydantoin compound (Ii).

Further, the process of this embodiment may include the separation of enantiomers of substituted spiro-hydantoin compound (If) to provide the substituted spiro-hydantoin enantiomers (Ig) and (Ih)

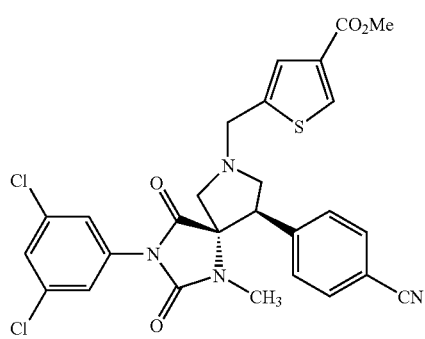
(Ig)

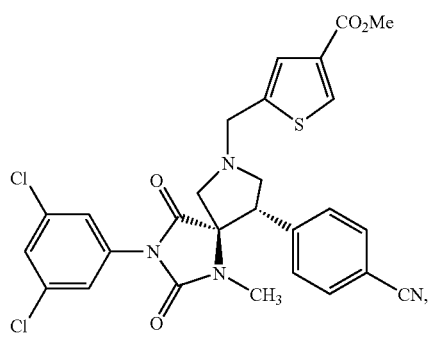
(Ih)

prior to step b, and then in step b, hydrolyzing either the enantiomer (Ig) or the enantiomer (Ih) to afford the respective enantiomer of the substituted spiro-hydantoin compound (Ii). These enantiomers of the substituted spiro-hydantoin compound (Ii) are represented by substituted spiro-hydantoin compound (Ij):

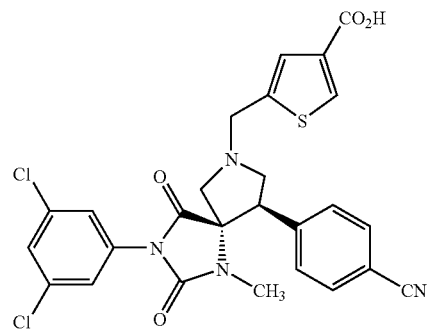
(Ij)

and spiro-hydantoin compound (Ik):

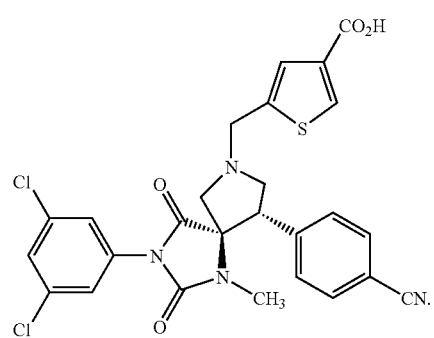
(Ik)

Alternatively, the substituted spiro-hydantoin compound (Ii) may be separated to provide the substituted spiro-hydantoin compounds (Ij) and (Ik) as separate enantiomeric components. The process of this embodiment is suitable for preparing 5-[(5S,9R)-9-(4-Cyanophenyl)-3-(3,5-dichlorophenyl)-1-methyl-2,4-dioxo-1,3,7-triazaspiro[4.4]non-7-ylmethyl]-thiophene-3-carboxylic acid.

In another preferred embodiment, the process of this invention is directed towards the preparation of a substituted spiro-hydantoin compound having the formula IIc

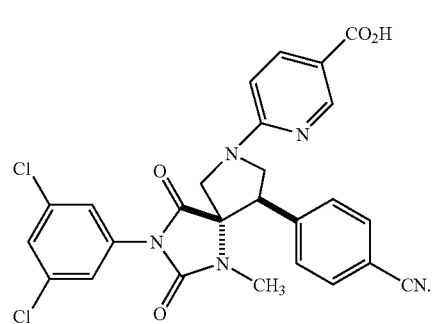
(IIc)

In this embodiment, the substituted spiro-hydantoin compound (IIc) is prepared by:

a) reacting the methylene precursor compound, and the N-substituted glycine compound (IVb) having the formula:

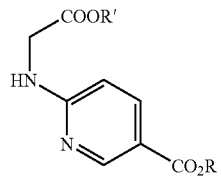
(IVb)

with alkene compound (IIIa) of formula

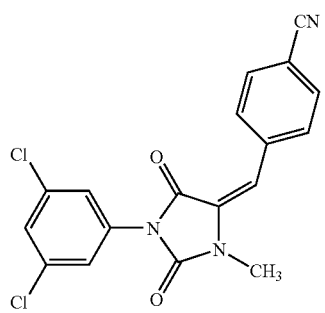
(IIIa)

to afford substituted spiro-hydantoin compound (IIf) of formula

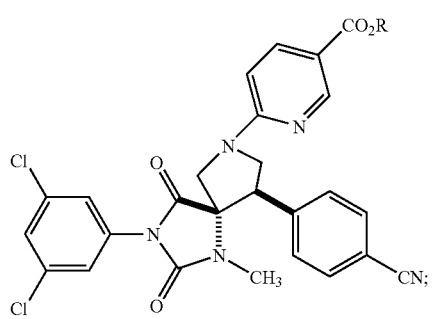
(IIf)

b) hydrolyzing the ester of the substituted spiro-hydantoin compound (IIf) to afford the substituted spiro-hydantoin compound (IIc). Preferably the ester group R is an alkyl group such as methyl or t-butyl.

Further, the process of this embodiment may include the separation of enantiomers of substituted spiro-hydantoin compound (IIf) to provide the substituted spiro-hydantoin enantiomers (IIg) and (IIh):

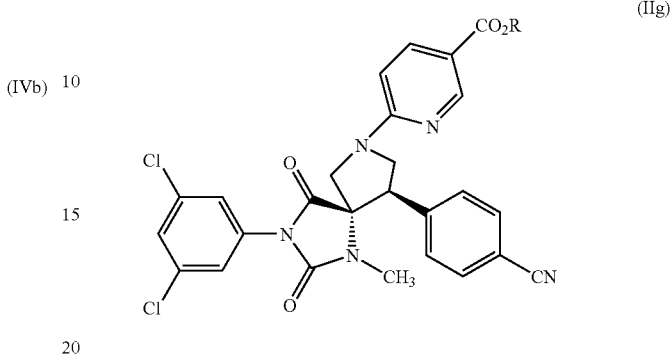
(IIg)

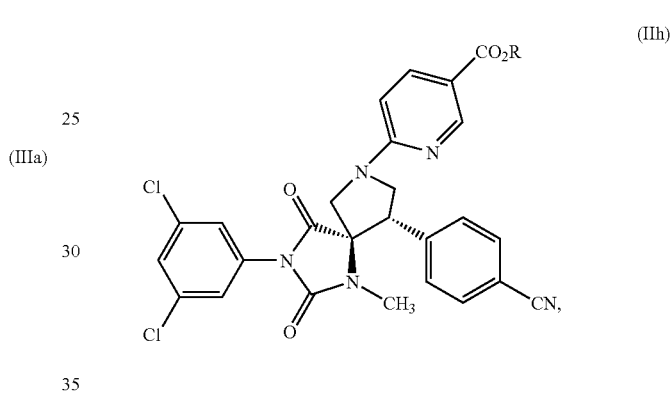
(IIh)

prior to step b, and then in step b, hydrolyzing either the enantiomer (IIg) or the enantiomer (IIh) to afford the substituted spiro-hydantoin compounds (IId) or (IIe), respectively. Alternatively, the substituted spiro-hydantoin compound (IIc) may be separated to provide the substituted spiro-hydantoin compounds (IId) and (IIe) as separated enantiomers. The substituted spiro-hydantoin compound (IId) is preferred. The process of this embodiment is suitable for preparing 6-[(5S,9R)-9-(4-cyanophenyl)-3-(3,5-dichlorophenyl)-1-methyl-2,4-dioxo-1,3,7-triazaspiro[4.4]non-7-yl]nicotinic acid.

For the process of this invention, starting materials are commercially available or can be readily prepared by one or ordinary skill in the art. Solvents, temperatures, pressures, starting materials having the desired groups, and other reaction conditions, may be readily selected as appropriate by one of ordinary skill in the art. The process can be scaled up in order to prepare larger quantities of the substituted spiro-hydantoin compound (II), such as in a commercial production facility.

Utility

Compounds of formula II (including crystalline and non-crystalline forms of compounds having formula IId), their prodrugs, salts and solvates thereof, prepared by any process, including the instant inventive process, are LFA-1 antagonists and inhibit the LFA-1/ICAM interaction. The present inventive compounds have utility in treating various inflammatory diseases and disorders associated with the action of LFA-1 and/or ICAMs, particularly LFA-1:ICAM-1. The term "Leukointegrin/ICAM-associated condition" is used herein for ease of reference to refer to those diseases or disorders that are associated with the action or levels of LFA-1, and/or ICAM-1, ICAM-2, or ICAM-3. As used herein, the term "treating" includes prophylactic and therapeutic uses and thus includes the alleviation of symptoms of a Leukointegrin/ICAM-associated condition in a patient, the improvement of an ascertainable measurement associated with such a condition, or the prevention of such a condition or its symptoms. The term "patient" refers to a mammal, preferably a human.

In view of their inhibition activity, the inventive compounds may be used to treat conditions involving the activation, co-stimulation, or infiltration of T-cells and/or leukocytes, including without limitation, conditions involving the influx of leukocytes in the skin, peritoneum, synovium, lung, kidney, and heart. These compounds may be used to treat conditions resulting from a response of the specific or non-specific immune system in a patient.

Leukointegrin/ICAM-associated conditions that may be treated with the instant inventive compounds include acute or chronic graft vs host reactions (e.g., pancreatic islet allograft); and acute or chronic transplant rejection (e.g., kidney, liver, heart, lung, pancreas, bone marrow, cornea, small bowel, skin allografts, skin homografts, heterografts, and/or cells derived from such organs). Additionally, these compounds may be useful in treating inflammatory conditions including, but not limited to, multiple sclerosis, rheumatoid arthritis, psoriatic arthritis, osteoarthritis, osteoporosis, diabetes (e.g., insulin dependent diabetes mellitus or juvenile onset diabetes), cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis (acute or chronic), multiple organ injury syndrome (e.g., secondary to septicemia or trauma), myocardial infarction, atherosclerosis, stroke, reperfusion injury (e.g., due to cardiopulmonary bypass or kidney dialysis), acute glomerulonephritis, vasculitis, thermal injury (i.e., sunburn), necrotizing enterocolitis, granulocyte transfusion associated syndrome, and/or Sjogren's syndrome.

The instant inventive compounds may be used in treating inflammatory conditions of the skin. Such conditions include, without limit, eczema, atopic dermatitis, contact dermatitis, urticaria, schleroderma, psoriasis, and dermatosis with acute inflammatory components.

The present inventive compounds, may also be used in treating allergies and respiratory conditions. Such conditions include, without limit, asthma, pulmonary fibrosis, allergic rhinitis, oxygen toxicity, emphysema, chronic bronchitis, acute respiratory distress syndrome, and any chronic obstructive pulmonary disease (COPD).

The present inventive compounds may be useful in treating hepatitis infection, including hepatitis B and hepatitis C.

Further, the inventive compounds may be useful in treating autoimmune diseases and/or inflammation associated with autoimmune diseases. Such diseases include, without limit, organ-tissue autoimmune diseases (e.g., Raynaud's syndrome), autoimmune thyroiditis, uveitis, systemic lupus erythematosis, Addison's disease, autoimmune polyglandular disease (also known as autoimmune polyglandular syndrome), and Grave's disease.

The instant inventive compounds may be useful in treating metastases or as an adjunct to minimize toxicity with cytokine therapy in the treatment of cancers.

The present inventive compounds may be useful in treating a number of conditions These conditions include, without limit, hypogonadism, frailty, sexual dysfunction, wasting, such as wasting syndromes associated with cancer and AIDS, and anemia. These compounds further have utility in treating cancers, including but not limited to cancers of the breast, brain, skin, ovary, endometrium, bladder, prostate, lung, colon, lymphatic system, liver and kidney. Other conditions include, without limit, hirsutism, acne, seborrhea, alopecia, fibroids, hyperpilosity, cachexia, polycystic ovarian syndrome, anorexia, contraception, drug withdrawal syndrome, pregnancy termination, and benign prostate hypertrophy. The aforementioned compounds may also be useful as antiangiogenic agents, as well as being useful as inhibitors of protein prenyltransferases, particularly farnesyltransferase and the prenylation of the oncogene protein Ras. Accordingly, these compounds may be useful for treating and/or preventing the diseases and disorders referred to in WO 01/45704, incorporated herein by reference.

The present inventive compounds may be particularly useful in treating acute or chronic graft vs host reactions, acute or chronic transplant rejection, multiple sclerosis, rheumatoid arthritis, psoriatic arthritis, osteoarthritis, osteoporosis, diabetes, cystic fibrosis, inflammatory bowel disease, irritable bowel syndrome, Crohn's disease, ulcerative colitis, Alzheimer's disease, shock, ankylosing spondylitis, gastritis, conjunctivitis, pancreatis, multiple organ injury syndrome, myocardial infarction, atherosclerosis, stroke, reperfusion injury, acute glomerulonephritis, vasculitis, thermal injury, necrotizing enterocolitis, granulocyte transfusion associated syndrome, Sjogren's syndrome, eczema, atopic dermatitis, contact dermatitis, urticaria, schleroderma, psoriasis, asthma, pulmonary fibrosis, allergic rhinitis, oxygen toxicity, emphysema, chronic bronchitis, acute respiratory distress syndrome, chronic obstructive pulmonary disease (COPD), hepatitis B, hepatitis C, organ-tissue autoimmune disease, autoimmune thyroiditis, uveitis, systemic lupus erythematosis, Addison's disease, autoimmune polyglandular disease, and Grave's disease. The present inventive compounds may be even more particularly useful in treating acute or chronic transplant rejection, rheumatoid arthritis, osteoarthritis, diabetes, asthma, inflammatory bowel disease, psoriasis, and chronic obstructive pulmonary disease.

When used as anti-inflammatory agents, the present inventive compounds may be administered prior to the onset of, at, or after the initiation of inflammation. When used prophylactically, these compounds are preferably provided in advance of any inflammatory response or symptom (for example, prior to, at, or shortly after the time of an organ or tissue transplant but in advance of any symptoms of organ rejection). Administration of the compounds may prevent or attenuate inflammatory responses or symptoms.

The present invention also provides pharmaceutical compositions capable of treating the above-referenced diseases and disorders, The inventive compositions may optionally contain other therapeutic agents and may be formulated with at least one pharmaceutically acceptable carrier or diluent. Such a formulation may employ, for example, conventional solid or liquid vehicles or diluents, as well as pharmaceutical additives of a type appropriate to the mode of desired administration (for example, excipients, binders, preservatives, stabilizers, flavors, etc.), according to techniques such as those well known in the art of pharmaceutical formulation.

The instant inventive compounds may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal administration via aerosol or inhalation include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a patient of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and the particular condition sought to be treated and its severity. Preferred subjects for treatment include animals, most preferably mammalian species such as humans, and domestic animals such as dogs, cats, horses, and the like, subject to Leukointegrin/ICAM associated conditions and/or subject to any of the above-referenced diseases and disorders.

The inventive compounds and compositions may be employed alone or in combination with each other and/or other suitable therapeutic agents useful in treating diseases and disorders referenced above, for example, where the second drug has the same or different mechanism of action than the present compounds. Exemplary of such other therapeutic agents include anti-inflammatory agents, antibiotics, anti-viral agents, anti-oxidants, and agents used to treat respiratory conditions such as COPD and asthma.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, Enbrel®, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), methotrexate (FK506), integrin antagonists (e.g., alpha-4 beta-1, alpha-V-beta-3), cell adhesion inhibitors, interferon gamma antagonists, prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, therapies for the treatment of irritable bowel syndrome (e.g., Zelmac®, Zelnorm®, and Maxi-K® openers such as those disclosed in U.S. Pat. No. 6,184,231 B1), or NF-κB inhibitors (such calphostin, CSAIDs, and quinoxalines as disclosed in U.S. Pat. No. 4,200,750); disassociated steroids; chemokine receptor modulators (including CCR1, CCR2, CCR3, CCR4, and CXCR2 receptor antagonists); secretory and cytosolic phospholipase A2 inhibitors, glucocorticoids, salicylates, nitric oxide, and other immunosuppressants; and nuclear translocation inhibitors, such as deoxyspergualin (DSG).

The inventive compounds may be used in combination with other agents used to treat respiratory conditions such as asthma, COPD, and allergic rhinitis, such as β-adrenergic agonists (such as albuterol, terbutaline, formoterol, salbutamol, salmeterol, bitolterol, pilbuterol, and fenoterol); corticosteroids (such as beclomethasone, triamcinolone, budesonide, fluticasone, flunisolide, dexamethasone, prednisone, and dexamethasone); leukotriene antagonists (e.g., Accolate [Zafirlukast®], and Singulair [Montelukast®]); Muscarinic M3 cholinergic antagonists (e.g., Spiriva®), PDE 4 inhibitors (e.g. rolipram, cilomilast [Ariflo®], piclamilast, or roflumilast), histamine $H_1$ antagonists, Allegra® (fexofenadine), Claritin® (loratidine), and/or Clarinex® (desloratidine).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

The inventive compounds also may be used in combination with anti-diabetic agents, such as biguanides (e.g. metformin), glucosidase inhibitors (e.g. acarbose), insulins (including insulin secretagogues or insulin sensitizers), meglitinides (e.g. repaglinide), sulfonylureas (e.g., glimepiride, glyburide and glipizide), biguanide/glyburide combinations (e.g., glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

In addition, the inventive compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196–2210 [1997]), PDE2 inhibitors, PDE3 inhibitors (such as revizinone, pimobendan, or olprinone), PDE4 inhibitors (referenced above), PDE7 inhibitors, or other PDE inhibitors such as dipyridamole, cilostazol, sildenafil, denbutyline, theophylline (1,2-dimethylxanthine), ARFLO™ (i.e., cis-4-cyano-4-[3-(cyclopentyloxy)-4-methoxyphenyl]cyclohexane-1-carboxylic acid), arofyline, C-11294A, CDC-801, BAY-19–8004, cipamfylline, SCH351591, YM-976, PD-189659, mesiopram, pumafentrine, CDC-998, IC-485, and KW-4490.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); K$^+$ channel modulators such as $I_{Ach}$ inhibitors and inhibitors of the $K_v1$ subfamily of K$^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, and amiloride.

The inventive compounds may also be useful in combination with antiangiogenic agents, such as compounds that are inhibitors of VEGF receptors, or in conjunction with antitumor agents such as paclitaxel, adriamycin, epothilones, cisplatin, and carboplatin. Examples of anticancer and other cytotoxic agents that may be used in combination with the inventive compounds include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416; and prenyl-protein transferase inhibitors as found in WO 97/30992 and WO 98/54966.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The substituted spiro-hydantoin compounds the present invention having formula II that are described in the examples herein, have been tested in assay(s) described below and have shown a measurable level of activity as inhibitors of LFA-1 and/or ICAM-, as well as having a low risk of drug-drug interaction and high metabolic stability.

H1-HeLa Adhesion Assay

H1-Hela cells were released from their growth flask using versene (Invitrogen, Carlsbad, Calif.). Following centrifugation, the cells were resuspended in growth medium: DMEM (Invitrogen), 10% fetal calf serum (Hyclone, Logan, Utah), 1% Pen-Strep (Invitrogen), and 1% L-glutamine (Invitrogen) and plated for growth at 5,000 cells/well in a 96-well plate.

The next day, HSB-2 cells were divided to $2 \times 10^5$/ml in growth medium: RPMI 1640 (Invitrogen), 10% FCS, 1% Pen-Strep, and 1% L-glutamine. The next day (day three), the cells were centrifuged at 534×g for 8 minutes, washed, and resuspended in HBSS at $5 \times 10^7$/ml. Calcein-AM (10 μM; Molecular Probes, Eugene, Oreg.) and 100 nM phorbol myristate acetate (PMA; SIGMA, St. Louis, Mo.) were added to the labeling and activation mix. Following incubation at 37° C. for 30 minutes, ten ml of HBSS (Invitrogen) was added and the cells centrifuged as above. The cell pellet was then resuspended and counted.

While the HSB-2 cells were labeling, the medium was aspirated from the H1-HeLa cells and the plates washed once with HBSS, followed by the addition of 50 μl of HBSS. An additional 50 μl of HBSS containing compound solution, DMSO, or anti-CD18 antibody was then added to each well. To the H1-HeLa cells were added 200,000 HSB-2 cells/well in 100 μl, followed by incubation in the dark for 30 minutes. The wells were then washed three times to remove the unbound cells. A fluorescence plate reader was then used to determine the number of bound HSB-2 cells. The percent inhibition due to the compound was calculated using the vehicle control as 0% inhibition and the antibody blocked adhesion as 100% inhibition.

HUVEC Adhesion Assay

On day 1, human umbilical vein endothelial cells (HUVEC) (passage 3, Clonetics, San Diego, Calif.) were placed into a T-75 flask containing EGM bullet kit media (Clonetics) for growth. When the HUVEC were 90% confluent (typically day 4), 96-well tissue culture plates were coated with 100 μl/well of 2.5 μg/ml mouse Type IV collagen (Trevigen, Gaithersburg, Md.) diluted in 0.1 M acetic acid. Following incubation for at least three hours, the collagen was removed and the plate washed three times with HBSS. The HUVEC flask was trypsinized, and HUVEC were plated on the collagen coated wells at 1250 cells/200 μl/well for use four days later. Twenty hours prior to use, the medium was removed and cells were stimulated with 200 μl of 10 nM PMA in EGM. When the cells were 90% confluent the PMA-containing medium was removed, the wells were washed with HBSS, and 50 μl of HBSS was added to the wells. An additional 50 μl containing compound solution, DMSO or blocking anti-CD18 was then added to each well.

Peripheral blood mononuclear cells (PBMCs) were isolated from EDTA-treated blood collected from normal healthy volunteers. Specifically, 20 ml of EDTA-treated blood was diluted with EDTA-containing RPMI, and PBMCs separated by layering the blood over 12 mls of Lympho Separation Media (Mediatech, Herndon, Va.), and centrifuging at 720×g for 25 min. The cells that accumulated at the interface (PBMCs) were transferred to a clean 50 ml conical tube, diluted with RPMI and pelleted by spinning at 615×g for 10 min. The PBMCs were then washed twice with growth media, resuspended in 10 ml of growth media and added to a T-225 flask.

Phytohemagglutinin (PHA) blasts were generated by stimulating peripheral blood mononuclear cells (PBMCs) with PHA (Sigma), and after 3 days the cells were diluted 1 to 6 in growth media containing rIL-2 (0.01 μg/ml final concentration). PHA blasts were grown for one week, and split to $5 \times 10^5$/ml the day before the HUVEC adhesion assay was conducted. The next day, the cells were centrifuged at 534×g for 8 minutes, washed, and resuspended in HBSS at $5 \times 10^7$/ml. For activation and labeling, Calcein-AM (10 μM) and 100 nM PMA were added and the cells incubated at 37° C. for 30 minutes. Following the addition of ten ml of HBSS, the cells were centrifuged, resuspended, and counted.

To the HUVEC cells were added 200,000 labeled and activated PHA blasts/well in 100 μl, followed by incubation in the dark for 30 minutes. To remove unbound cells, the wells were washed three times with HBSS. A fluorescence plate reader was used to determine the number of PHA blasts that were bound. The percent inhibition due to the compound was calculated with the vehicle control set at 0% inhibition and the antibody-blocked adhesion set at 100% inhibition.

CYP Assay

The CYP assay was conducted according to the procedure in *Drug Metabolism and Disposition*, 28, 1440–1448 (2000).

Microsomal Liver Assay

Mouse and rat liver microsomes were purchased from XenoTech LLC (Kansas City, Kans.), and human liver microsomes were obtained from BD Gentest (Woburn, Mass.).

The oxidative metabolism in liver microsomes of various species was studied under the following condition: 3 μM test compound (organic solvent content <0.1%), 1 mg/mL microsomal proteins, 1 mM β-nicotinamide adenine dinucleotide phosphase (β-NADPH), 100 mM phosphate buffer (pH 7.4), and 6.7 MM magnesium chloride. The reaction (n=3) was initiated by the addition of NADPH followed by incubation at 37° C. for 20 min. Aliquots of samples (0.1 mL) were taken at 0, 5, and 20 min, and the reaction was quenched by the addition of three volumes of acetonitrile. Samples were stored at −20° C. until analysis.

The rate of oxidation in liver microsomes was determined from the following equation: rate (nmol/min/mg protein) $=k^* C_0 / C_{protein}$, where k (1/min) is the turnover rate constant estimated from non-linear regression of the percent compound remaining (y)-time (t) curve using the equation $y = y_0 * \exp(-k^* t)$; $C_0$ is initial drug concentration (μM), and $C_{protein}$ is microsomal protein concentration (mg/mL).

Rates of metabolism are "binned" (classified) as follows:

| Rate (nmol/min/mg) | Clearance Estimate |
|---|---|
| 0–0.10 | low |
| 0.10–0.20 | intermediate |
| 0.20–0.30 | high |

EXAMPLES

The following examples illustrate embodiments of the inventive process, and are not intended to limit the scope of the claims. For ease of reference, the following abbreviations are used herein:

Abbreviations

EtOH=ethanol
HCl=hydrochloric acid
HPLC=high pressure liquid chromatography
kg=kilogram
L=liter
mol=mole
TBME=t-butyl methyl ether
THF=tetrahydrofuran

Preparation 1

3-(3,5-dichlorophenyl)-1-methylimidazolidine-2,4-dione

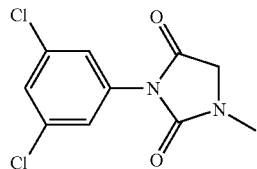

Triethylamine (0.78 kg, 7.75 mol) was added in 15–30 minutes with stirring to a thin suspension of sarcosine ethylene hydrochloride (1.00 kg, 6.51 mol) in dichloromethane (6.00 L). After stirring at room temperature for 1.5–2 hours, the mixture was filtered to remove the resulting triethylamine hydrochloride salt. The salt cake was washed with dichloromethane (2.00 L). The filtrate was cooled to 0–5° C.

A solution of 3,5-dichlorophenyl isocyanate (1.47 kg, 7.81 mol) in dichloromethane was prepared at 20–25° C. The solution was added to the above cooled filtrate slowly in 30–60 minutes. The temperature was maintained below 10° C. during the addition. After the addition, the mixture was stirred at 20–25° C. for 12–14 hours. The completeness of the reaction was followed by HPLC. Upon reaction completion, TBME (16.00 L) was added in one portion. The resulting suspension was stirred at 20–25° C. for 2–3 hours and was then filtered. The filter cake was washed with TBME (4.50 L) and dried at maximum 40° C. to a constant weight. A suspension of the above filter cake in water (17.0 L, 10 L/kg input) was prepared and stirred at 20–25° C. for at least 16 hours. The suspension was filtered and the filter cake was washed with water (3×1.36 L) and dried at maximum 40° C. to a constant weight. 3-(3,5-dichlorophenyl)-1-methylimidazolidine-2,4-dione (1.52 kg, 90%) was obtained as a white crystalline solid. mp=202–204° C. $^1$H NMR (DMSO-$d_6$): 7.66 (1H, m), 7.51 (2H, m), 4.10 (2H, s), 3.35 (3H, s). $^{13}$C NMR (DMSO-$d_6$): 8 Carbons (169.30, 155.00, 134.98, 134.15, 127.59, 125.30, 51.75, 29.79). Anal. Calcd for $C_{10}H_8Cl_2N_2O_2$: C, 46.35; H, 3.11; N, 10.81; Cl, 27.36. Found: C, 46.43; H, 2.92; N, 10.73; Cl, 27.33.

Preparation 2

(E)-4-((1-(3,5-dichlorophenyl)-3-methyl-2,5-dioxoimidazolidin-4-ylidene)methyl)benzonitrile

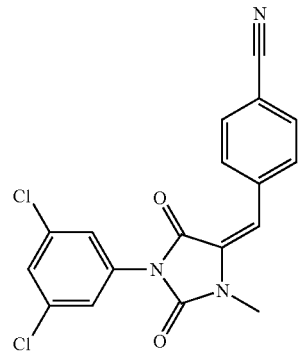

A mixture of 3-(3,5-dichlorophenyl)-1-methylimidazolidine-2,4-dione (1.00 kg, 3.86 mol), 4-cyanobenzaldehyde (0.70 kg, 5.79 mol), and pyrrolidine (0.27 kg, 3.86 mmol) was refluxed in EtOH (13.00 L) for 20–24 hours at a temperature of 78° C. The completeness of the reaction was followed by HPLC. Upon reaction completion, the suspension was cooled to 65° C. and THF (4.33 L) was added in 5–10 minutes. The suspension was cooled to 20–25° C. in 3–4 hours and was then filtered. The filter cake was washed with EtOH (4×2.00 L) and dried at maximum 40° C. to a constant weight. (E)-4-((1-(3,5-dichlorophenyl)-3-methyl-2,5-dioxoimidazolidin-4-ylidene)methyl)benzonitril (1.24 kg, 86%) was obtained as a fluffy, yellowish crystalline solid. mp=239–241° C. $^1$H NMR (DMSO-$d_6$): 8.07 (2H, d, J=8.3 Hz), 7.86 (2H, d, J=8.4 Hz), 7.72 (1H, m), 7.59 (2H, m), 6.72 (1H, s), 3.35 (3H, s). $^{13}$C NMR (DMSO-$d_6$): 14 Carbons (159.80, 151.48, 137.64, 133.83, 133.70, 131.80, 130.80, 130.68, 127.71, 125.51, 118.83, 114.48, 110.32, 26.72). Anal. Calcd for $C_{18}H_{11}Cl_2N_3O_2$: C, 58.08; H, 2.97; N, 11.29; Cl, 19.05. Found: C, 58.14; H, 2.72; N, 11.14; Cl, 19.15.

Example 1

4-[(5S*,9R*)-7-Benzyl-3-(3,5-dichlorophenyl)-1-methyl-2,4-dioxo-1,3,7-triazaspiro[4.4]non-9-yl]-benzonitrile

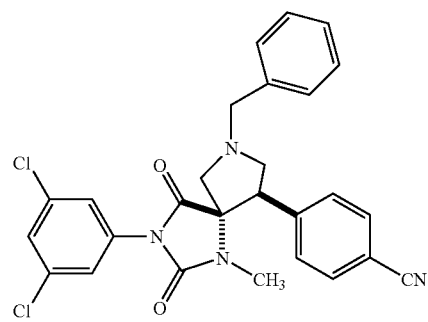

A mixture of (E)-4-((1-(3,5-dichlorophenyl)-3-methyl-2,5-dioxoimidazolidin-4-ylidene)methyl)benzonitrile (1.05 g, 2.82 mmol), hexamethylenetetramine (0.395 g, 2.82 mmol), N-benzylglycine (1.17 g, 7.05 mmol), toluene (5 ml), and 1-methyl-2-pyrrolidinone (NMP, 10 ml) was heated to 140° C. The extent of reaction was monitored by HPLC. After 72 hours, the reaction had stopped short of completion. The ratio of product to starting material ((E)-4-((1-(3,5-dichlorophenyl)-3-methyl-2,5-dioxoimidazolidin-4-ylidene)methyl)benzonitrile) was 1.36:1. Mass spectra of the mixture indicated the presence of the desired product. The mixture was washed with water and extracted into toluene. The impure product was obtained as an oil. Comparison of the product obtained to authentic material was made by HPLC. The ratio of the desired (5S, 9R) isomer to the undesired was 19:1.

Preparation 3

Preparation of tert-butyl 6-chloronicotinate

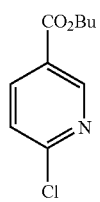

A mixture of 6-chloronicotinic acid (12.0 g, 76 mmol) and thionyl chloride (65 mL) was heated at reflux for 3.0 h. The excess thionyl chloride was removed under reduced pressure, and the residual liquid was diluted with dichloromethane (20 mL) and then added to a solution of tert-butyl alcohol (71 mL, 760 mmol) in dichloromethane (40 mL). To the mixture was added triethylamine (31.7 mL, 760 mmol) and N,N-dimethylpyridine (0.5 g, 4.0 mmol), and the reaction mixture was stirred overnight (14 h) at reflux under nitrogen. The solution was diluted with dichloromethane (200 mL), washed with a saturated aqueous solution of sodium bicarbonate (3×100 mL), washed with water (3×100 mL), and dried over anhydrous sodium sulfate. Concentration under reduced pressure provided Preparation 3 (11.4 g, 70.3%) as a yellow solid. The product had an analytical HPLC retention time=3.18 min. (Column: YMC ODS 4.6×50 mm (4 min.); Solvent A=10% MeOH, 90% H$_2$O, 0.2% H$_3$PO$_4$; Solvent B=90% MeOH, 10% H$_2$O, 0.2% H$_3$PO$_4$) and a LCMS M$^{+1}$=214. The purity of the product was about 96%. The major impurity was the iso-propyl 6-chloronicotinate with an analytical HPLC retention time=2.88 min. and a LC/MS M$^{+1}$=200.

Preparation 4

4-[(5S,9R)-3-(3,5-Dichlorophenyl)-1-methyl-2,4-dioxo-1,3,7-triazaspiro[4.4]non-9-yl]-benzonitrile

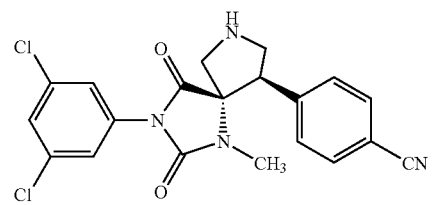

Preparation 4 was prepared according to Example 15A in WO 03/029245.

Example 2a tert-butyl 6-[(5S*,9R*)-9-(4-cyanophenyl)-3-(3,5-dichlorophenyl)-1-methyl-2,4-dioxo-1,3,7-triazaspiro[4.4]non-7-yl]nicotinate

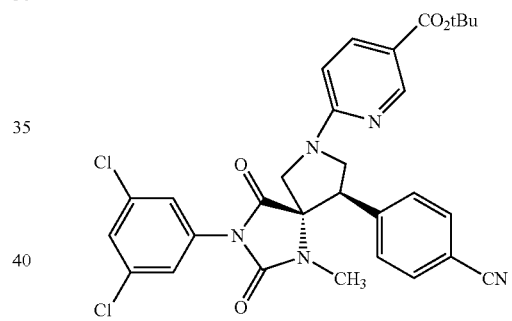

To a mixture of the Preparation 2 (14.5 g, 34.9 mmol) and t-butyl 6-chloronicotinate (8.0 g, 35.6 mmol) in dimethylacetamide (50 mL) was added diisopropylethylamine (11.3 g, 87.3 mmol). The reaction mixture was stirred at 112° C. for 18 h under nitrogen. After cooling, the mixture was added slowly to ice water (200 mL) with stirring. After an additional 10 min. of stirring, the resulting precipitate was collected by vacuum filtration and was washed with water (3×20 mL). The crude product was dried and purified by silica gel chromatography eluting with a 5% and a 10% mixture of ethyl acetate in dichloromethane to give Example 1 as yellow solid (15.8 g, 76.5%). The product had an analytical HPLC retention time=3.91 min. (Column: YMC ODS 4.6×50 mm (4 min.); Solvent A=10% MeOH, 90% H$_2$O, 0.2% H$_3$PO$_4$; Solvent B=90% MeOH, 10% H$_2$O, 0.2% H$_3$PO$_4$) and a LCMS M$^{+1}$=592. $^1$H-NMR (500 MHz, CDCl$_3$) δ=1.59 (s, 9H); 3.26 (s, 3H); 3.95–4.25 (m, 5H); 6.47 (d, 1H, J=9.0 Hz); 6.81–6.82 (m, 2H); 7.29–7.30 (m, 1H); 7.40(d, 2H, J=8.0 Hz); 7.70 (d, 2H, J=8.0 Hz); 8.08(dd, 1H, J=9.0 and 2.4 Hz); and 8.82(d, 1H, J=2.4 Hz).

Example 2b tert-butyl 6-[(5S,9R)-9-(4-cyanophenyl)-3-(3,5-dichlorophenyl)-1-methyl-2,4-dioxo-1,3,7-triazaspiro[4.4]non-7-yl]nicotinate

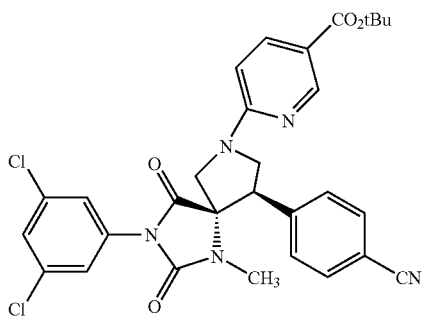

A 3-necked flask was charged with 6-chloronicotinic acid (53.0 g, 336 mmol), 4-(dimethylamino)-pyridine (3.03 g, 24.6 mmol), and tetrahydrofuran (350 mL). The contents of the flask was heated to 62.5° C. and a solution of di-tert-butyl dicarbonate (200.2 g, 917 mmol) in tetrahydrofuran (240 mL) was slowly added over a period of 4.6 h. The contents of the flask were maintained at 62.5° C. for approximately 1 h and then cooled to 21° C. A portion of the solution (219 mL), which contained tert-butyl 6-chloronicotinate (16.4 g, 76.8 mmol), was mixed with 1 N NaOH (150 mL) and methyl tert-butyl ether (150 mL) at 21° C. To this mixture was charged 4-[(5S,9R)-3-(3,5-Dichlorophenyl)-1-methyl-2,4-dioxo-1,3,7-triazaspiro[4.4]non-9-yl]-benzonitrile semi (+)-DTTA salt (37.4 mmol, 61.5 mmol). After mixing for 10 minutes, a phase split was performed, the aqueous layer was discarded and the organic layer was distilled under atmospheric pressure. After 220 mL of distillate was collected, 220 mL of methyl tert-butyl ether was charged back and the distillation was resumed. After an additional 250 mL of distillate was collected, 100 mL of n-methyl-2-pyrrolidinone was charged and the distillation was continued until the pot temperature rose to 90° C. Diisopropylethyl amine (27 mL, 155 mmol) was then charged and the mixture was heated at 110° C. for approximately 17 h. A portion of the crude reaction mixture (48 mL) was transferred into a separate funnel and was extracted twice with 3.4:1 heptane:cyclohexane (31 mL). The top layers were discarded and the bottom layer was extracted three times with a mixture of methyl tert-butyl ether (36 mL) and $H_2O$ (24 mL). The bottom aqueous layers were discarded. To the top layer was added methyl tert-butyl ether (40 mL) and was filtered back to a distillation flask. After most of methyl tert-butyl ether was distilled off, the mixture was diluted to a total volume of 169 mL with 1:1 methyl tert-butyl ether:isopropyl alcohol. p-Toluenesulfonic acid (0.358 g) was then added to this solution and was dissolved upon gently heating. The solution was then cooled and stirred until crystals appeared. A second charge of p-toluenesulfonic acid (0.424 g) was added and the slurry was further stirred at 21° C. for 30 minutes before it was filtered and washed twice with 25 mL of 1:1 methyl tert-butyl ether:isopropyl alcohol. The product (3.34 g, 86% yield) was isolated as white crystals and was dried in a vacuum oven at 40° C.

Example 3

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

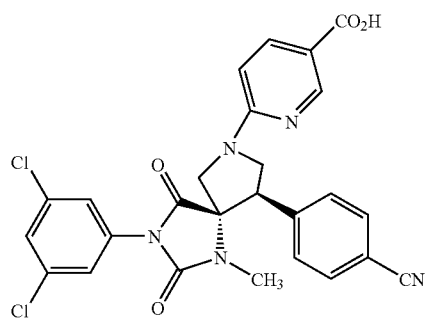

To the solution of Example 2a (15.5 g, 26.2 mmol) in dichloromethane (50 mL) was added trifluoroacetic acid (50 mL) dropwise between 0–5° C. with stirring. After the addition was complete, the ice water bath was removed, and the mixture was stirred at room temperature for 3.5 h. The solvent was then removed under reduced pressure, and the residue obtained was diluted with dichloromethane (400 mL) and water (100 mL). After stirring for 10 min., the pH of the aqueous layer was adjusted to 8–9 with a saturated aqueous solution of sodium bicarbonate. The mixture was stirred for 15 min., and the pH was rechecked to assure basicity. The pH was then adjusted to 4–5 with a 1N aqueous solution of hydrochloric acid. After stirring for 15 min., the organic layer was collected, and the aqueous layer was extracted with dichloromethane (50 mL). The organic phases were combined, washed with brine (100 mL), and dried over anhydrous sodium sulfate. Concentration under reduced pressure gave the crude solid product, which was dissolved in chloroform (55 mL) and stirred gently overnight at room temperature. The mixture was stirred for 30 min. in an ice bath, and the resulting precipitate was collected by vacuum filtration. The white crystals were washed with cold chloroform (2×5 mL) and dried under reduced pressure to give Example 3 (11.49 g). A second crop of Example 3 (0.6 g, total yield: 86.1%) was obtained by concentration of the mother liquor and processing it as outlined earlier. The product had an analytical HPLC retention time=3.23 min. (Column: YMC ODS 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$) and a LCMS $M^+$=536. $^1$H-NMR (500 MHz, DMSO-d6) δ=3.20(s, 3H); 4.01(d, 1H, J=12.4 Hz); 4.18–4.21(m, 3H); 4.37 (t, 1H, J=9.3 Hz); 6.69 (d, 1H, J=8.5 Hz); 6.81 (s, 2H); 7.48 (d, 2H, J=8.5 Hz); 7.64 (s, 1H); 7.89(d, 2H, J=8.3 Hz); 8.03 (d, 1H, J=8.8 Hz) 8.69(s, 1H); and 12.59(s, 1H).

Example 4

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

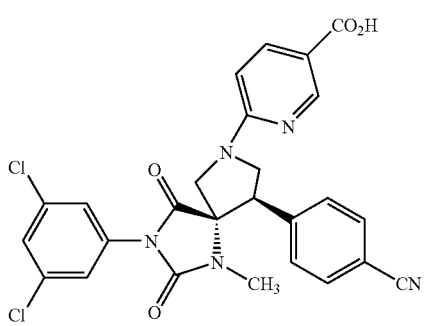

To a flame-dried 2 L, 4-neck round bottom flash equipped with a magnetic stir bar, a reflux condenser, and an internal temperature probe, was added 6-chloronicotinic acid (47.5 g, 0.301 mol) with stirring. Dichloromethane (500 mL) was added followed by 1,1,1,3,3,3-hexamethyldisilazane (48.0 mL, 0.226 mol). Next, chlorotrimethylsilane (1.7 mL, 0.013 mol) was added, and the reaction mixture was heated at a vigorous reflux with rapid stirring (a steady stream of nitrogen was used to drive off the ammonium chloride salt). The dichloromethane level was maintained as needed. After 4.5 h, the reaction mixture was clear with a reddish-orange color. The solution was cooled to room temperature, the reflux condenser was replaced with a 250 mL bump-trap attached to a vacuum line, and the reaction mixture was concentrated under reduced pressure with rapid stirring to give a tan solid (the internal temperature was maintained between 10–20° C. with a heat gun). The resulting solid was dried under high vacuum for 1 h, maintaining the temperature of the flask at room temperature.

To the 2 L, 4-neck round bottom flask containing the trimethylsilyl ester equipped with a reflux condenser, a magnetic stir bar, and an internal temperature probe was added anhydrous dimethylacetamide (600 mL) with stirring. To the solution was added Preparation 4 (70.0 g, 0.169 mol) followed by diisopropyldiethylamine (73.3 mL, 0.421 mol) and dimethylaminopyridine (1.03 g, 8.50 mmol). The reaction mixture was heated at 90° C. for 18 h, cooled to 27° C., and quenched with anhydrous methanol (140 mL) (During the quench, the internal temperature rose to 34° C.). The mixture was stirred for 20 min. at room temperature, the reflux condenser was replaced with a bump trap (250 mL) attached to a vacuum line, and the volatiles were removed under reduced pressure while heating a 41° C. for 1.5 h. The resulting dimethylacetamide solution was cooled to room temperature and was slowly added to rapidly stirring water (600 mL). After 400 mL had been added, the product started to precipitate out. After all of the water had been added, a thick reddish gum was observed in the bottom of the flask. The DMA/water layer was transferred into an Erlenmeyer flask, stirred for 20 min., and filtered under reduced pressure through a coarse fritted funnel. The off-white solid was washed with water several times. The reddish gum was dissolved in 350–400 mL of DMA and added slowly to 400 mL of water with rapid stirring. The resulting suspension was stirred for 25 min., filtered under reduced pressure through a coarse fritted funnel, and the resulting off-white solid was washed with water several times. The solids were allowed to dry under reduced pressure in the fritted funnels overnight. The precipitate in the filtrates was collected by filtration under reduced pressure and air dried. The HPLC of all three samples was determined to be comparable, so all were combined to give 72 g of the product. The combined material was heated in a vacuum oven at 70° C. under reduced pressure for 72 h to give 71 g of Example 4 as an off-white solid. The compound was >98% pure by HPLC with a retention time=2.99 min. (Column: Chromolith SpeedROD 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$).

A suspension of Example 4 (65 g) in 1800 mL of chloroform was heated at a vigorous reflux using a heating mantle and a heat gun to form a solution (45 min.). To the dark red solution was added activated charcoal (6.5 g), and the mixture was heated at reflux for an additional 30 min. The reaction mixture was cooled to approximately 40° C. and filtered through a pad of Celite topped with a pad of activated charcoal (650 mL fritted funnel) with gentle warming of the fritted funnel and maintaining the product/charcoal solution temperature at ~40° C. After the filtration was complete, the Celite/charcoal was washed with chloroform (4×). The solution was concentrated under reduced pressure until ~500 g of the solution remained, while maintaining the internal temperature around room temperature. The volume of the filtrate was adjusted to 840 g with the addition of chloroform to give a 1 g product to 8 mL chloroform ratio. The homogeneous solution was stirred overnight at room temperature. The resulting fine white precipitate was collected by vacuum filtration to give 55 g of the product as a white crystalline solid. The product was dried in a vacuum oven at 120° C. under reduced pressure (house vacuum) for 19 h. Residual solvent analysis indicated that there was still 8.9% chloroform present. The material was then heated in a vacuum oven attached to a high vacuum pump at 110° C. for 15 h. to give 44.2 g (68%) as a white solid which was submitted as Example 4. Residual solvent analysis indicated that only 0.20% chloroform remained. Powder X-ray diffraction patterns and microscopy indicated that the material was crystalline. The product had a HPLC retention time of 2.99 min. (Column: Chromolith SpeedROD 4.6×50 mm (4 min.); Solvent A=10% MeOH, 90% $H_2O$, 0.2% $H_3PO_4$; Solvent B=90% MeOH, 10% $H_2O$, 0.2% $H_3PO_4$) with a LC/MS $M^{+1}$=536.

Example 5

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

Example 6

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

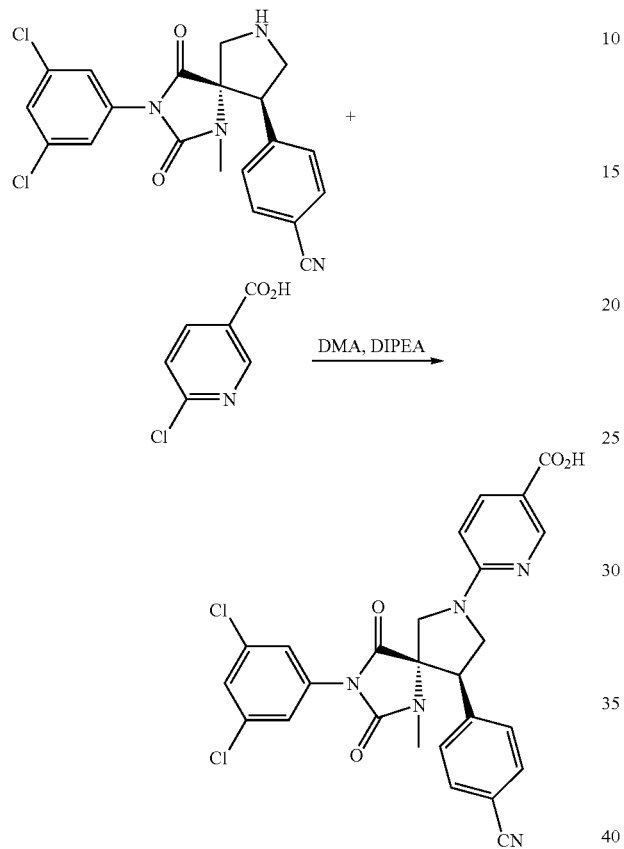

To a 250 mL round bottom flask was added with 6-chloronicotinic acid (2.35 g, 15 mmol), Preparation 4 (4.15 g, 10.0 mmol), dimethylacetamide (40 mL), and diisopropylethylamine (3.2 g, 25.0 mmol). After the reaction mixture was stirred at 110° C. for 30 hours under nitrogen, it was cooled to room temperature and was slowly added to ice water (200 mL) with stirring. The resulting white slurry was filtered by vacuum filtration and the product was washed with water (3×20 mL). The crude product was dried in vacuo at 60° C. for 16 hours to afford Example 6 as a white solid (4.6 g, 87%). The crude product was re-dissolved in chloroform (25 mL) and stirred overnight at room temperature then 4° C. for 30 minutes. The white crystals were collected by vacuum filtration, washed with cold chloroform (2×5 mL), and dried under vacuo at 60° C. to give Example 5 (2.95 g, 54% yield). A second crop of Example 5 (0.52 g) was obtained by concentration of the mother liquor. LCMS (M+1)$^+$=536. $^1$H-NMR (DMSO-D$_6$, 500 MHz) δ 8.68 (s, 1H), 8.31 (s, 1H), 8.00 (s, 2H), 7.90 (s, 1H), 7.63 (s, 2H), 6.84 (s, 2H), 4.37 (t, J=9.9 Hz, 1H), 4.16(d, J=9.9 Hz, 3H), 4.00(d, J=12.1 Hz, 1H), 3.19 (s, 3H); $^{13}$C-NMR (DMSO-D$_6$, 500 MHz) δ 170.81, 166.46, 158.01, 152.81, 150.37, 139.08, 137.81, 133.65, 132.88, 132.15, 128.83, 127.64, 124.46, 114.62, 110.73, 105.48, 48.03, 46.75, 45.24, 24.73.

To a 250 mL round bottom flask was charged with 6-iodonicotinic acid (373.3 mg, 1.5 mmol), Preparation 4 (414 mg, 1 mmol), dimethylacetamide (2 mL) and diisopropylethylamine (320 mg, 2.5 mmol). After the reaction mixture was stirred at 110° C. for 16 hours under nitrogen, it was cooled to room temperature and was slowly added to ice water (2 mL) with stirring. The resulting white slurry was filtered by vacuum filtration and the product was washed with water (3×2 mL). The crude product was dried in vacuo at 60° C. for 16 hours to afford Example 6 as a white solid (472 mg, 88%). The crude product was re-dissolved in chloroform (25 mL) and stirred overnight at room temperature then 4° C. for 30 minutes. The white crystals was collected by vacuum filtration, washed with cold chloroform (2×5 mL), and dried under vacuo at 60° C. to give Example 6 (347 mg, 75% yield). LCMS (M+1)$^+$=536. $^1$H-NMR (DMSO-D$_6$, 500 MHz) δ 8.68 (s, 1H), 8.31 (s, 1H), 8.00 (s, 2H), 7.90 (s, 1H), 7.63 (s, 2H), 6.84 (s, 2H), 4.37 (t, J=9.9 Hz, 1H), 4.16(d, J=9.9 Hz 3H), 4.00(d, J=12.1 Hz, 1H), 3.19 (s, 3H); $^{13}$C-NMR (DMSO-D$_6$, 500 MHz) δ 170.81, 166.46, 158.01, 152.81, 150.37, 139.08, 137.81, 133.65, 132.88, 132.15, 128.83, 127.64, 124.46, 114.62, 110.73, 105.48, 48.03, 46.75, 45.24, 24.73.

Example 7

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

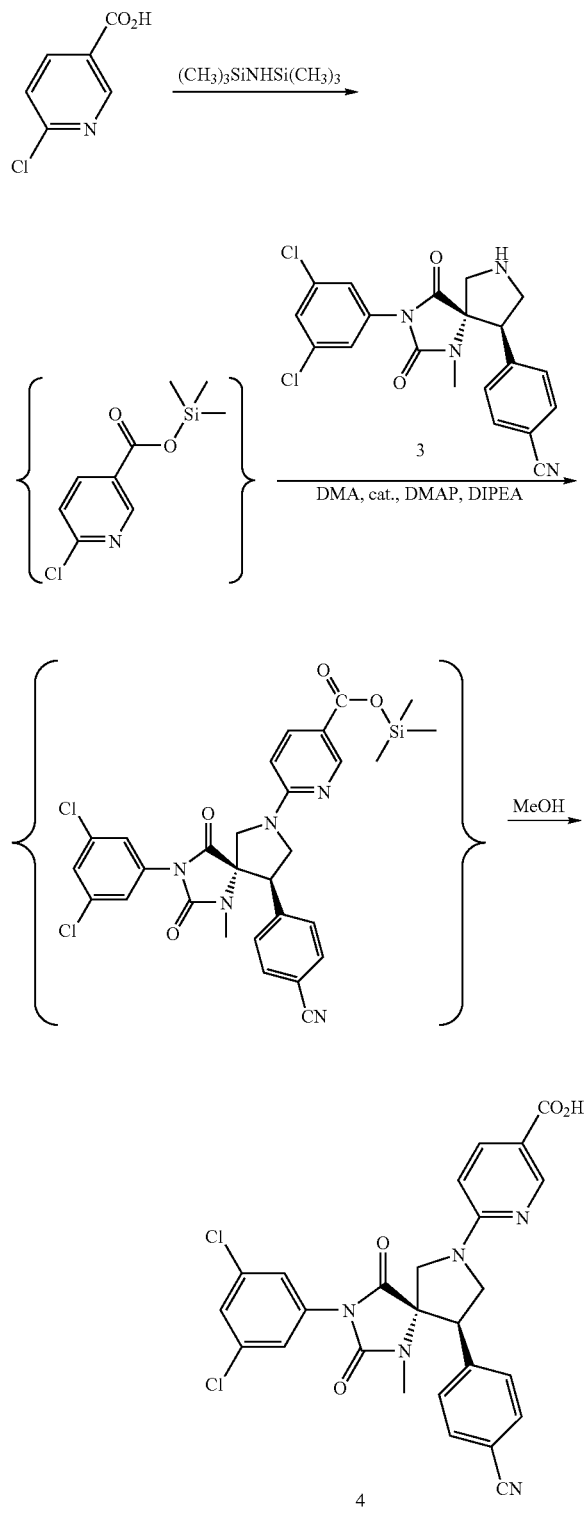

To a 2 L 3 neck round bottom flask was charged with 6-chloronicotinic acid (37.8 g, 0.24 mol), dichloromethane (360 mL), hexamethyldisilazane (28.61 g, 0.177 mol), and chlorotrimethylsilanel (1.11 g, 10 mmol). The slurry was refluxed under a nitrogen atmosphere for 3 hours until a light brown solution was obtained. The reaction mixture was cooled to room temperature and the solvent was removed under reduced pressure to afford a light brown syrup which solidified upon cooling.

To this flask was charged with Preparation 4 (49.68 g, 0.119 mol), dimethylacetamide (500 mL), and diisopropylethylamine (38.73 g, 0.299 mmol). After the reaction mixture was stirred at 90° C. for 18 hours under nitrogen, it was cooled to room temperature. Next, methanol (200 mL) was added with stirring. The temperature was raised from 25° C. to 35° C. The volatile solvents (MeOH and methyltrimethoxysilane) were removed under vacuo and the resulting mixture was slowly added to DI water (600 mL) with stirring. The resulting white slurry was filtered by vacuum filtration and the product was washed with water (3×20 mL). The product was dried to afford Example 7 as a white solid (62.88 g, 98%). LCMS (M+1)$^+$=536. $^1$H-NMR (DMSO-D$_6$, 500 MHz) δ 8.68 (s, 1H), 8.31 (s, 1H), 8.00 (s, 2H), 7.90 (s, 1H), 7.63 (s, 2H), 6.84 (s, 2H), 4.37 (t, J=9.9 Hz, 1H), 4.16(d, J=9.9 Hz, 3H), 4.00(d, J=12.1 Hz, 1H), 3.19 (s, 3H); $^{13}$C-NMR (DMSO-D$_6$, 500 MHz) δ 170.81, 166.46, 158.01, 152.81, 150.37, 139.08, 137.81, 133.65, 132.88, 132.15, 128.83, 127.64, 124.46, 114.62, 110.73, 105.48, 48.03, 46.75, 45.24, 24.73.

Example 8

6-[(5S,9R)-9-(4-cyanophenyl)-3-(3,5-dichlorophenyl)-1-methyl-2,4-dioxo-1,3,7-triazaspiro[4.4]non-7-yl]nicotinic acid

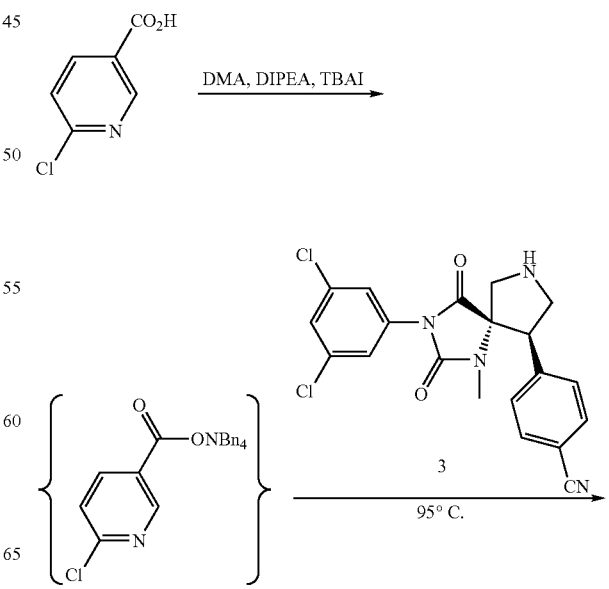

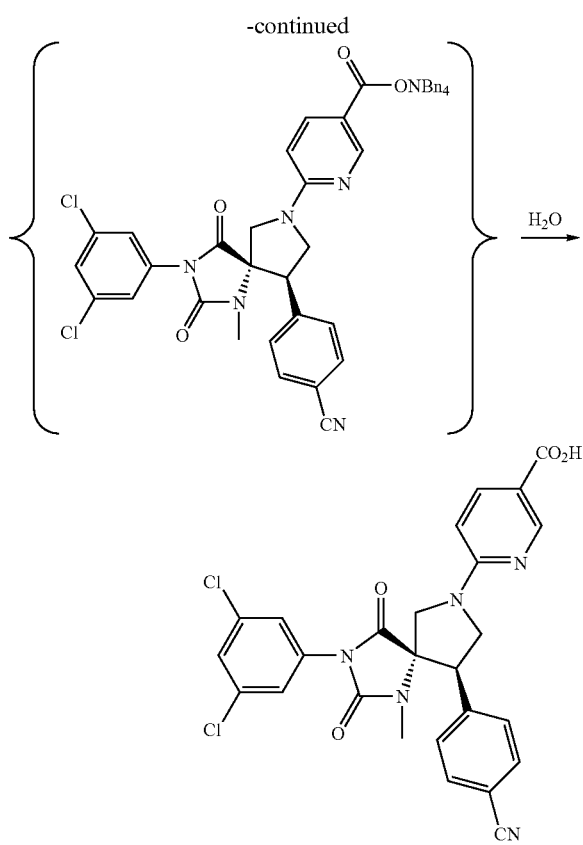

To a 250 mL round bottom flask was charged with 6-chloronicotinic acid (7.24 g, 45.9 mmol), dimethylacetamide (45 mL), diisopropylethylamine (7.61 g, 56.9 mmol), and tetrabutylammonium iodide (16.9 g, 45.9 mmol). The mixture was heated under a nitrogen atmosphere for 3 hours.

To the flask was added Preparation 4 (9.47 g, 22.8 mmol), and the reaction mixture was stirred at 95° C. for 30 hours under nitrogen, cooled to room temperature, and was slowly added to ice water (200 mL) with stirring. The resulting white slurry was filtered by vacuum filtration and the product was washed with water (3×20 mL). The product was dried in vacuo at 60° C. for 16 hours to afford Example 8 as a white solid (11.98 g, 98%). LCMS (M+1)$^+$=536. $^1$H-NMR (DMSO-D$_6$, 500 MHz) δ 8.68 (s, 1H), 8.31 (s, 1H), 8.00 (s, 2H), 7.90 (s, 1H), 7.63 (s, 2H), 6.84 (s, 2H) 4.37 (t, J=9.9 Hz, 1H), 4.16(d, J=9.9 Hz, 3H), 4.00(d, J=12.1 Hz, 1H), 3.19 (s, 3H) $^{13}$C-NMR (DMSO-D$_6$, 500 MHz) δ 170.81, 166.46, 158.01, 152.81, 150.37, 139.08, 137.81, 133.65, 132.88, 132.15, 128.83, 127.64, 124.46, 114.62, 110.73, 105.48, 48.03, 46.75, 45.24, 24.73.

Example 9

Crystal Forms of 6-[(5S,9R)-9-(4-cyanophenyl)-3-(3,5-dichlorophenyl)-1-methyl-2,4-dioxo-1,3,7-triazaspiro[4.4]non-7-yl]nicotinic acid Various crystal forms of the substituted spiro-hydantoin compound (IId) were prepared and unit cell data and other properties for these examples are tabulated in Tables 1a and 1b. the unit cell parameters were obtained from single crystal X-raycrystallographic analysis. A detailed account of unit cells can be found in Chapter 3 of Stout & Jensen, *X-Ray Structure Determination: a Practical Guide*, (MacMillian, 1968). The fractional atomic coordinates for the N-4 and H-1 forms are tabulated in Tables 2 and 3.

Crystals of the N-4 form was recrystallized from a butyl acetate solution at 80° C.

Crystals of the H-1 form were grown from 4:1 solution of PEG400:aqueous 0.1M NaH$_2$PO$_4$ in water, pH=7.

Crystals of the CHF-2 form were grown from chloroform solution.

Crystals of the hydrochloric acid salt form, H3.5-1, were prepared from an aqueous HCl and alcohol solution.

Crystals of the hydrochloric acid salt form, H4-1, were prepared from an ethanol solution containing 1.2 equivalents of HCl.

What is claimed is:

1. A compound according to formula II:

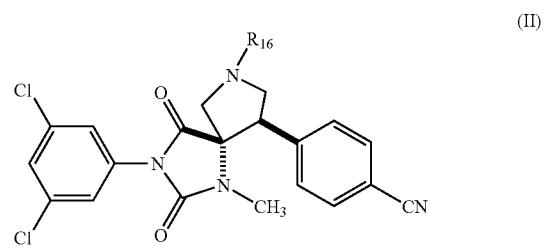

its enantiomers or pharmaceutically-acceptable salts, thereof, wherein:

R$_{16}$ is:

, , or ;

each R$_{17}$ is independently —OR$_{18}$, —NR$_{18}$R$_{19}$, —C(=O)R$_{18}$, —CO$_2$R$_{18}$, —C(=O)NR$_{18}$R$_{19}$, —NR$_{18}$C(=O)R$_{19}$, —NR$_{18}$C(=O)OR$_{19}$, —S(O)$_p$R$_{19}$, —NR$_{18}$SO$_2$R$_{19}$, and/or —SO$_2$NR$_{18}$R$_{19}$;

R$_{18}$ and R$_{19}$ are independently hydrogen, alkyl, substituted alkyl, cycloalkyl, and/or substituted cycloalkyl;

q is 1, 2, or 3; and p is 1 or 2.

2. The compound according to claim 1, its enantiomers or pharmaceutically-acceptable salts, thereof, wherein:

each R$_{17}$ is independently —OR$_{18}$, —C(=O)R$_{18}$, —CO$_2$R$_{18}$, and/or —C(=O)NR$_{18}$R$_{19}$; and R$_{18}$ and R$_{19}$ are independently hydrogen, alkyl, and/or substituted alkyl.

3. The compound according to claim 2, its enantiomers or pharmaceutically-acceptable salts, thereof, wherein q is 1.

4. The compound according to claim 3, its enantiomers or pharmaceutically-acceptable salts, thereof, wherein R$_{16}$ is

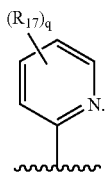

5. The compound according to claim 4, its enantiomers or pharmaceutically-acceptable salts, thereof, wherein $R_{16}$ is

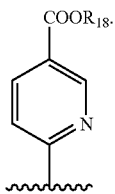

6. The compound according to claim 5, its enantiomers or pharmaceutically-acceptable salts, thereof, wherein $R_{18}$ is hydrogen.

7. The compound according to claim 1, its enantiomers or pharmaceutically-acceptable salts, thereof, wherein said compound (IId) has the formula:

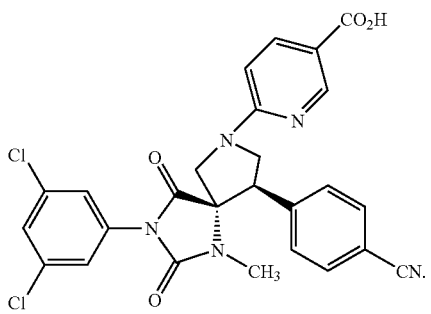

(IId)

8. A pharmaceutical composition comprising at least one compound according to claim 1 and a pharmaceutically acceptable carrier or diluent.

* * * * *

UNITED STATES PATENT AND TRADEMARK OFFICE
CERTIFICATE OF CORRECTION

PATENT NO. : 7,186,727 B2 Page 1 of 1
APPLICATION NO. : 11/301454
DATED : March 6, 2007
INVENTOR(S) : T.G. Murali Dhar et al.

It is certified that error appears in the above-identified patent and that said Letters Patent is hereby corrected as shown below:

In the Claims:

Col. 61, lines 1 to 8, change " 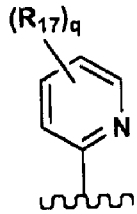 " to -- 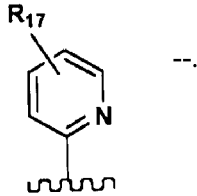 --.

Signed and Sealed this

Fifth Day of August, 2008

JON W. DUDAS
*Director of the United States Patent and Trademark Office*